US012083001B2

(12) United States Patent
Yamamoto

(10) Patent No.: US 12,083,001 B2
(45) Date of Patent: Sep. 10, 2024

(54) DISPOSABLE WEARING ARTICLE

(71) Applicant: Daio Paper Corporation, Ehime (JP)

(72) Inventor: Shohei Yamamoto, Ehime (JP)

(73) Assignee: Daio Paper Corporation, Ehime (JP)

( * ) Notice: Subject to any disclaimer, the term of this patent is extended or adjusted under 35 U.S.C. 154(b) by 992 days.

(21) Appl. No.: 16/967,260

(22) PCT Filed: Feb. 12, 2019

(86) PCT No.: PCT/JP2019/004809
§ 371 (c)(1),
(2) Date: Aug. 4, 2020

(87) PCT Pub. No.: WO2019/167601
PCT Pub. Date: Sep. 6, 2019

(65) Prior Publication Data
US 2020/0397627 A1    Dec. 24, 2020

(30) Foreign Application Priority Data

Feb. 28, 2018    (JP) .................................. 2018-034889

(51) Int. Cl.
*A61F 13/496*    (2006.01)
*A61F 13/15*    (2006.01)
(Continued)

(52) U.S. Cl.
CPC .... *A61F 13/4963* (2013.01); *A61F 13/49017* (2013.01); *A61F 13/49413* (2013.01);
(Continued)

(58) Field of Classification Search
CPC ............ A61F 13/4963; A61F 13/49017; A61F 13/494; A61F 13/49406; A61F 13/49413;
(Continued)

(56) References Cited

U.S. PATENT DOCUMENTS 5,752,947 A * 5/1998 Awolin ............... A61F 13/4753
604/385.04
2003/0093053 A1    5/2003 Een
(Continued)

FOREIGN PATENT DOCUMENTS

EP    1626690    2/2006
JP    11-514551    12/1999
(Continued)

OTHER PUBLICATIONS

International Search Report for PCT/JP2019/004809, issued Apr. 23, 2019.

*Primary Examiner* — Leslie A Lopez
*Assistant Examiner* — Quynh Dao Le
(74) *Attorney, Agent, or Firm* — Andrus Intellectual Property Law, LLP

(57)    ABSTRACT

A rising portion of a rising gather includes a main region having a first part extending toward the center in the width direction, a second part extending outward in the width direction from the tip of the first part, in the middle of the front-back direction including a crotch portion, and a support region composed of only a third part extending toward the center in the width direction, between the main region and a back fallen portion. The main region has a first gather elastic member attached to a tip end of the second part along the front-back direction. The support region has a second gather elastic member attached to the tip end of the third part along the front-back direction. The base edge side of the third part is a non-stretchable portion, and the third part has a layer that follows the second part of the main region.

10 Claims, 16 Drawing Sheets

(51) Int. Cl.
*A61F 13/49* (2006.01)
*A61F 13/494* (2006.01)

(52) U.S. Cl.
CPC .................. *A61F 13/15739* (2013.01); *A61F 2013/49093* (2013.01)

(58) Field of Classification Search
CPC ............. A61F 13/15739; A61F 13/475; A61F 13/496; A61F 13/49019; A61F 13/4942; A61F 2013/49093; A61F 2013/49493; A61F 2013/49433
See application file for complete search history.

(56) References Cited

U.S. PATENT DOCUMENTS

| | | | | |
|---|---|---|---|---|
| 2008/0065037 | A1* | 3/2008 | Konawa | A61F 13/4756 604/385.01 |
| 2011/0077613 | A1* | 3/2011 | Kurihara | A61F 13/4758 604/385.24 |
| 2016/0270985 | A1* | 9/2016 | Raycheck | A61F 13/55115 |
| 2016/0278996 | A1* | 9/2016 | Takahashi | A61F 13/4942 |
| 2018/0338874 | A1 | 11/2018 | Manabe et al. | |

FOREIGN PATENT DOCUMENTS

| | | | |
|---|---|---|---|
| JP | 2001-095844 | 4/2001 | |
| JP | 2006-525857 | 11/2006 | |
| JP | 2008-136756 | 6/2008 | |
| JP | 2009-285241 | 12/2009 | |
| JP | 2017-131613 | 8/2017 | |
| WO | WO-2016052330 A1 * | 4/2016 | ............. A61F 13/15 |
| WO | WO-2016152784 A1 * | 9/2016 | ............. A61F 13/49 |
| WO | 2017/056714 | 4/2017 | |

* cited by examiner

[FIG.1]
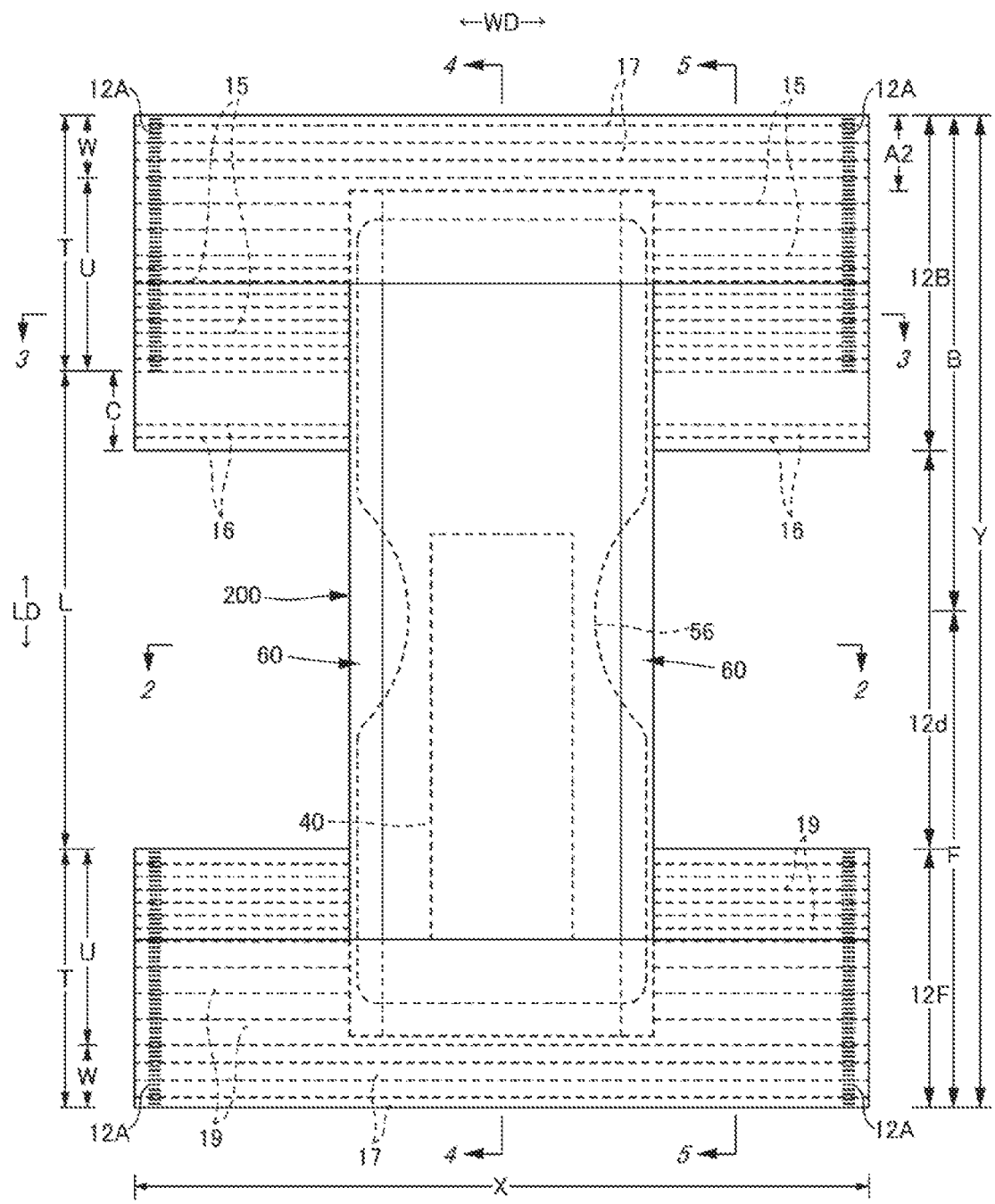

[FIG.2]
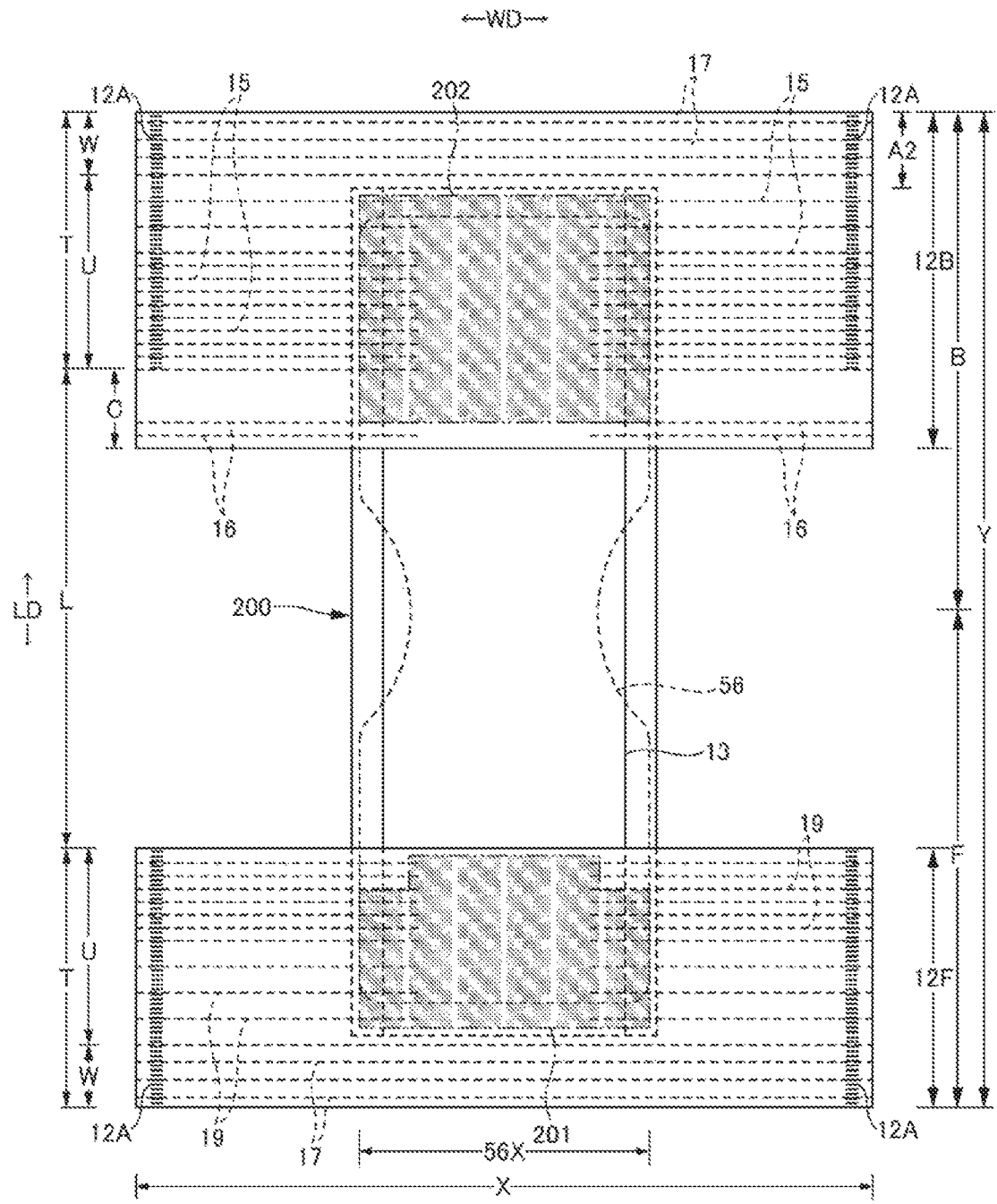

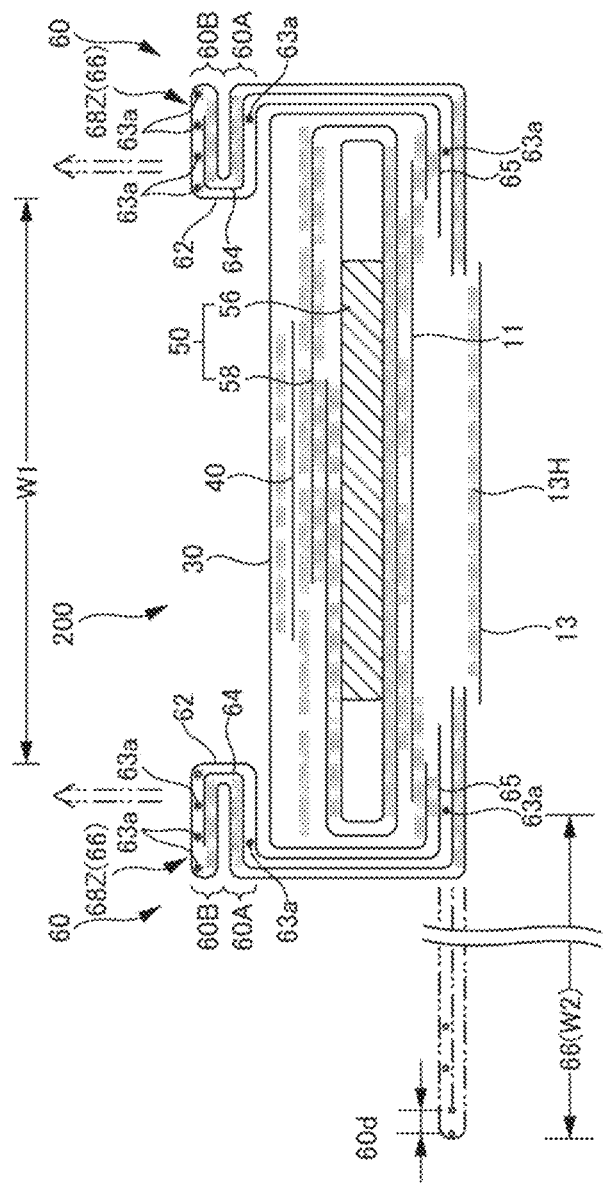

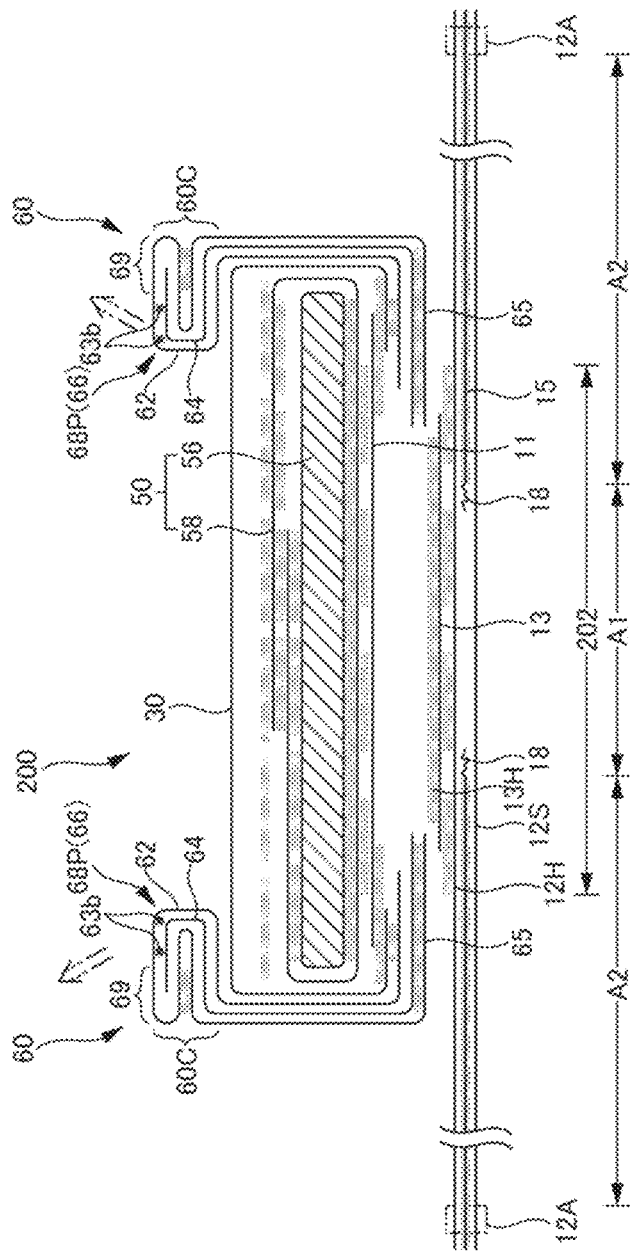

[FIG.5]
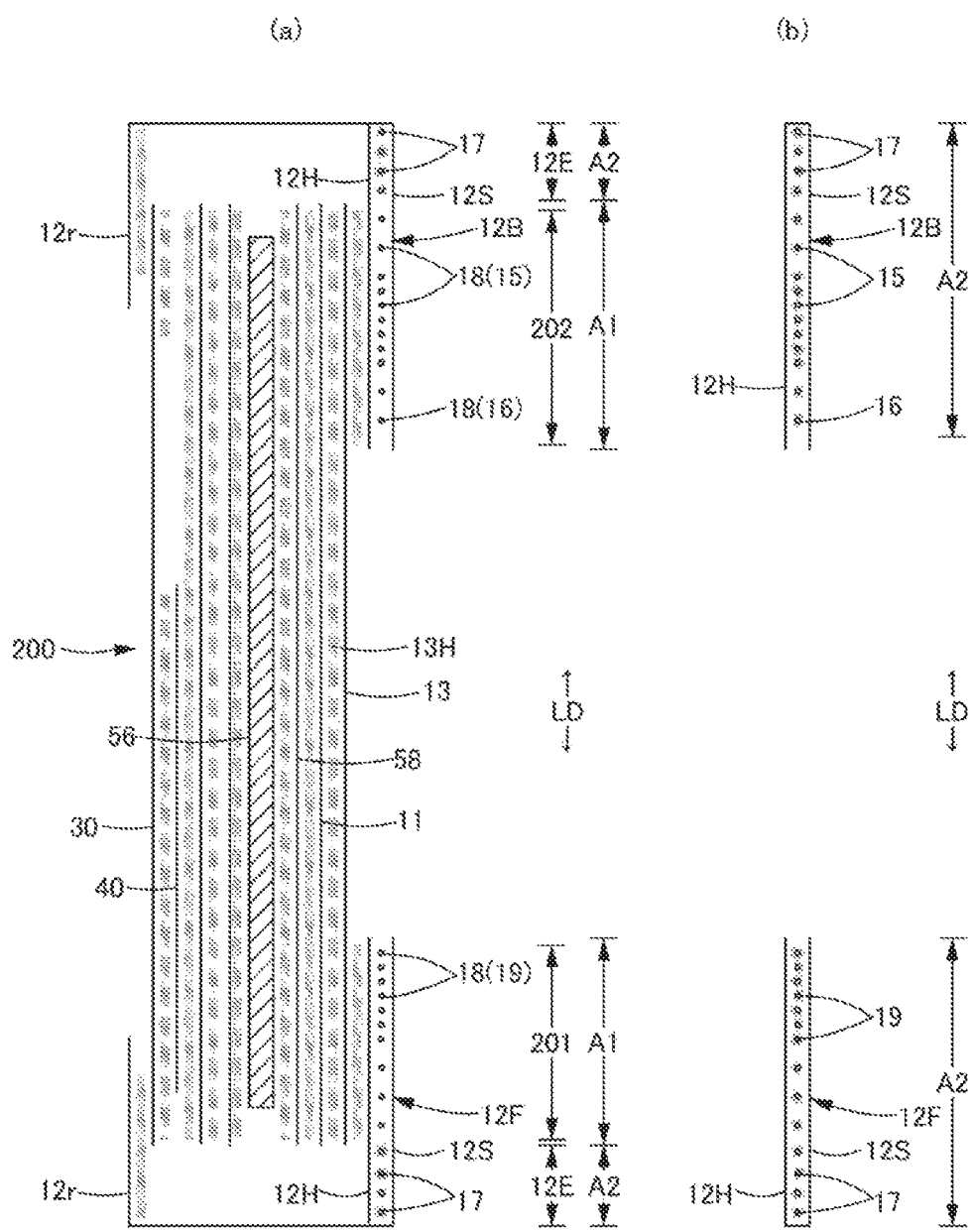

[FIG.6]
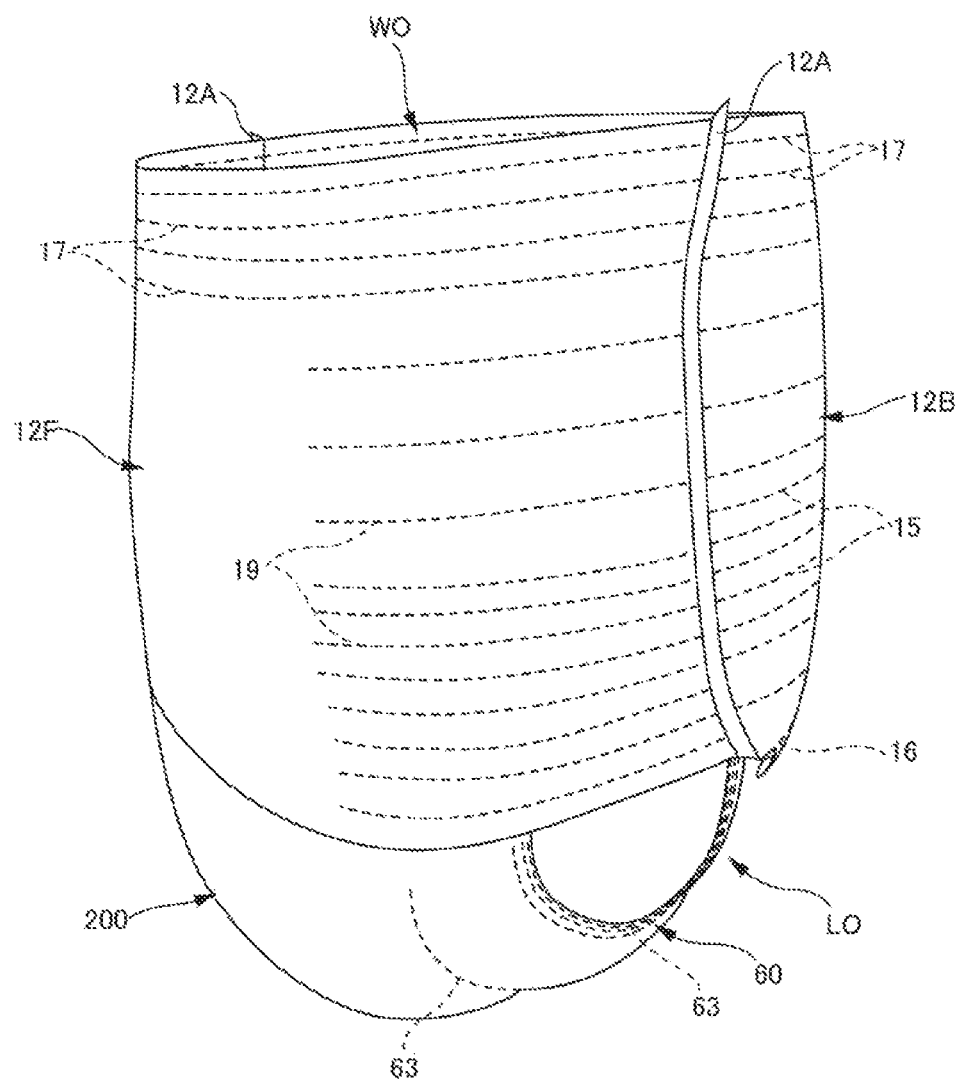

[FIG.7]
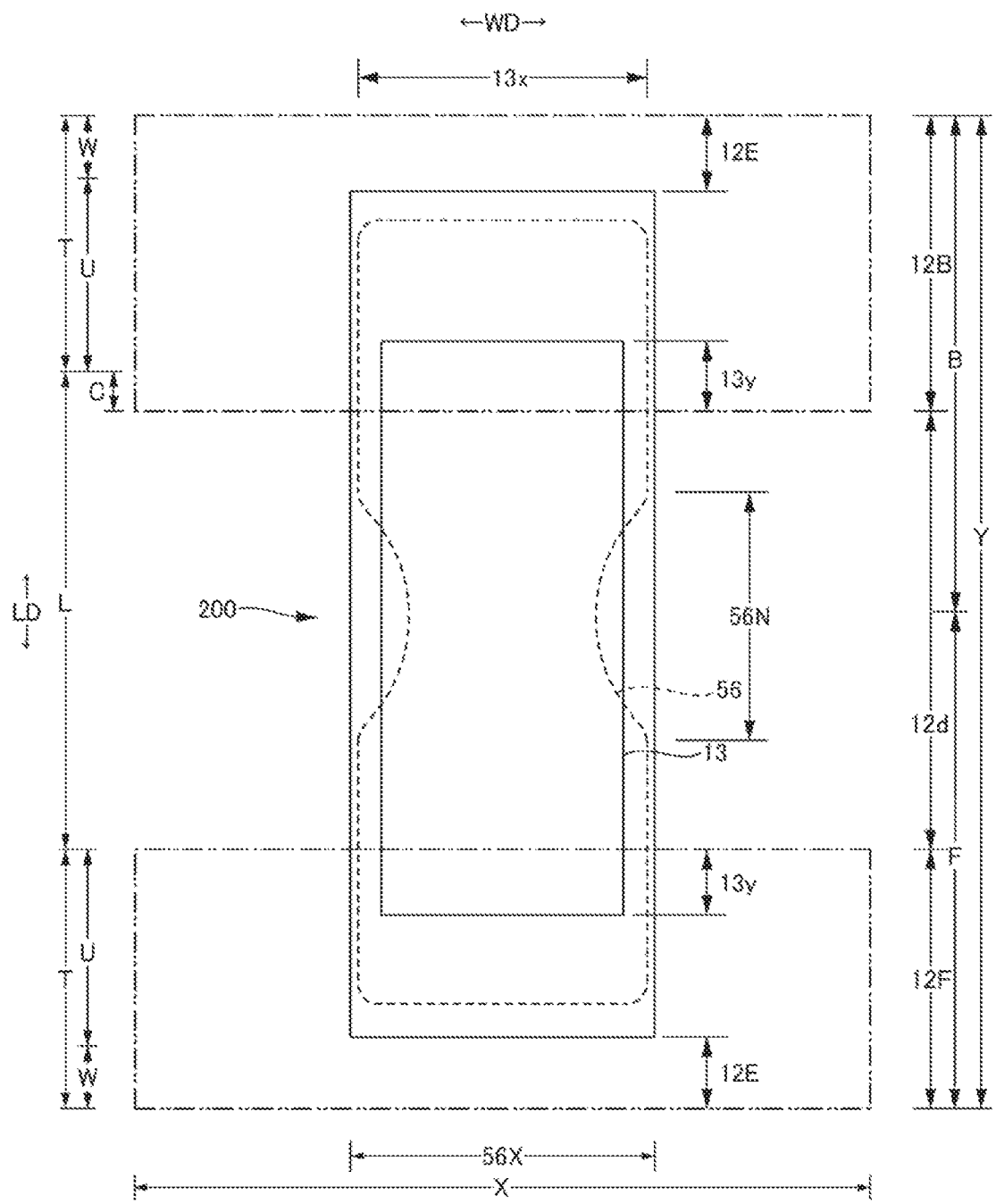

[FIG.8]
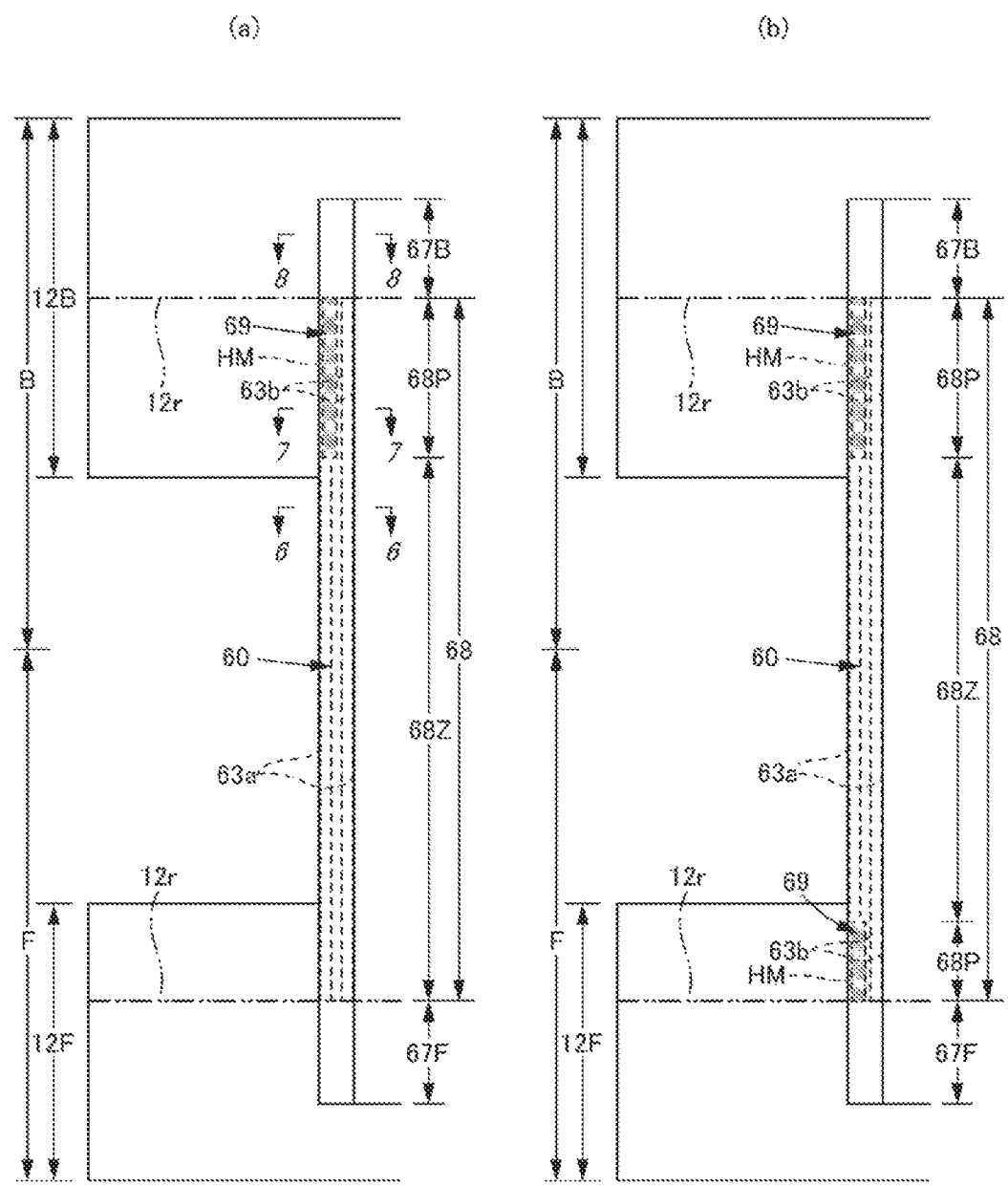

[FIG.9]
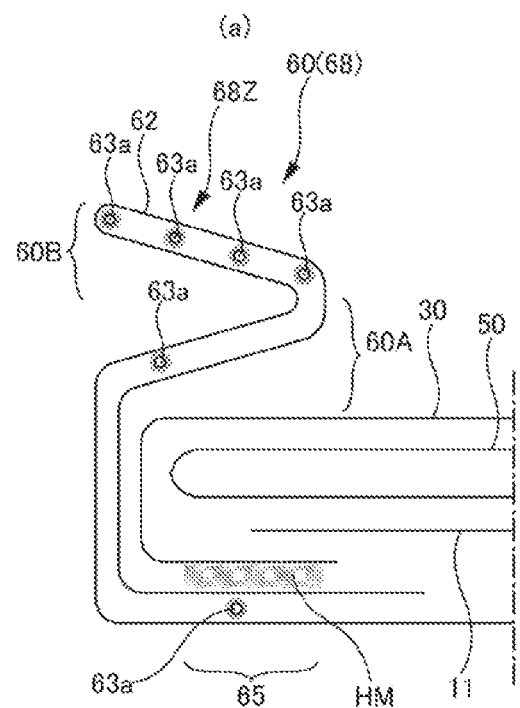
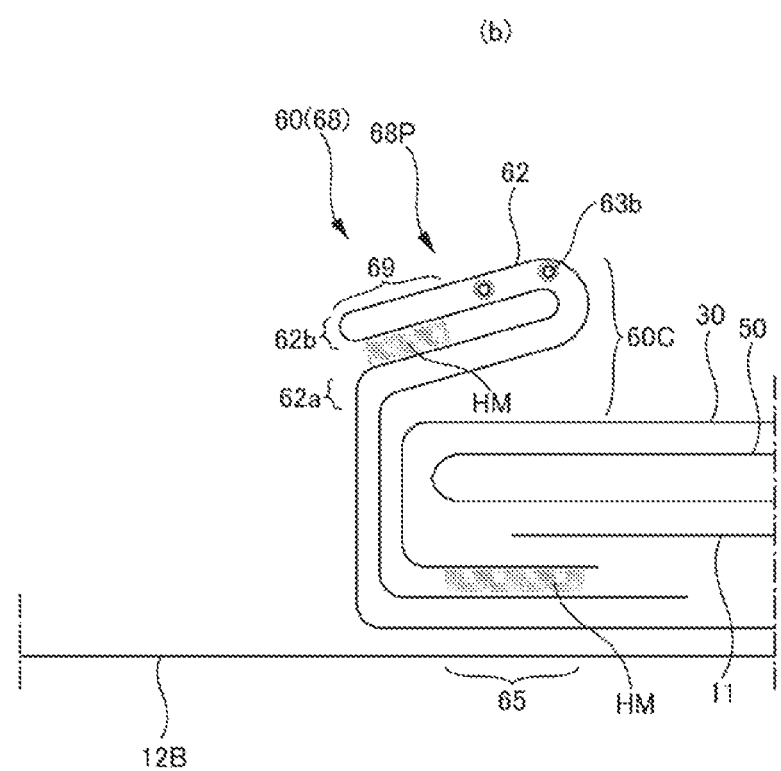

[FIG.10]
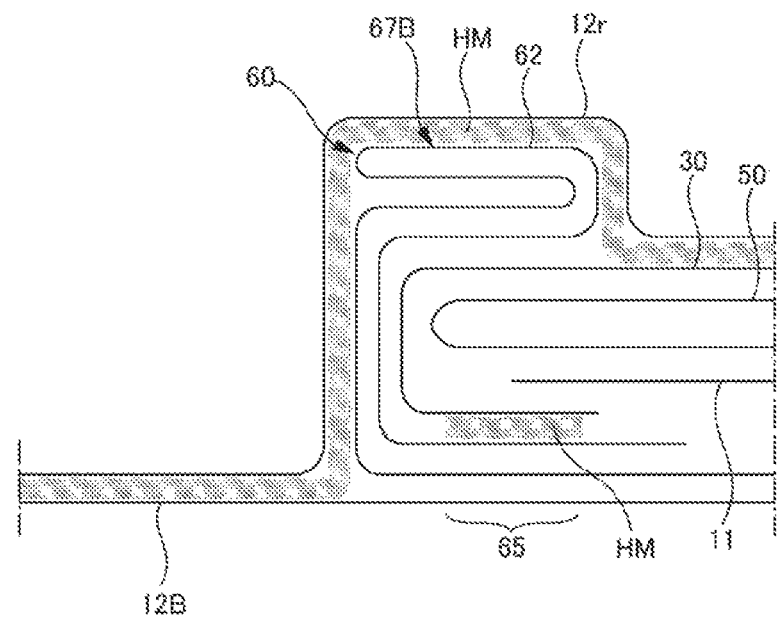

[FIG.14]
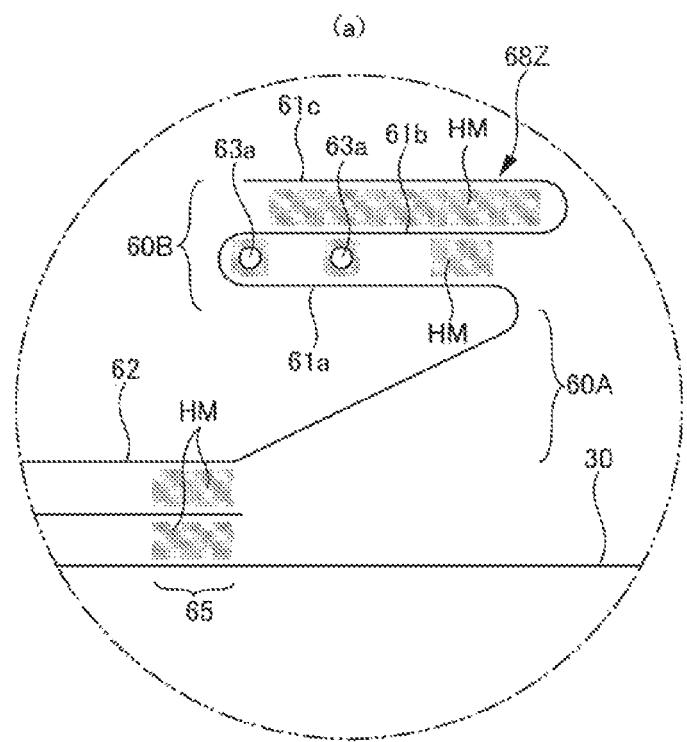
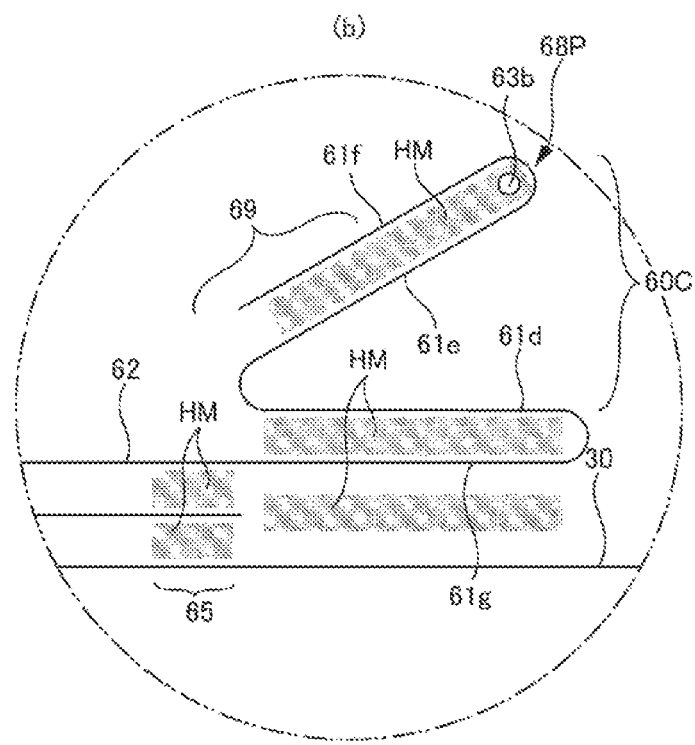

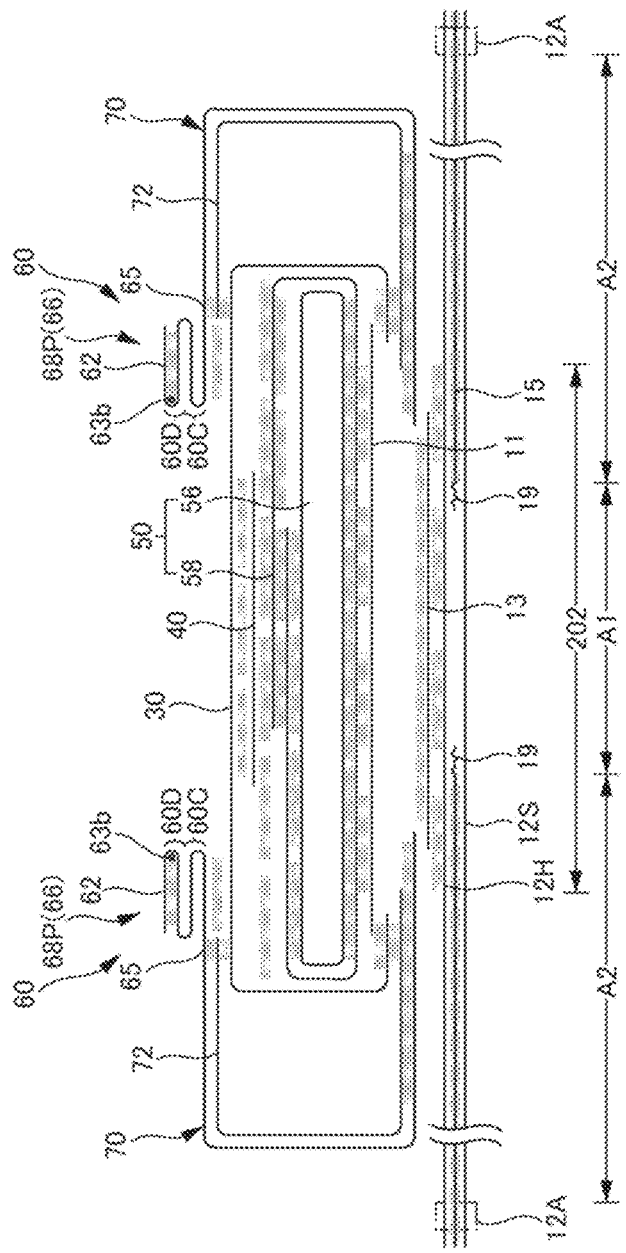

[FIG.16]
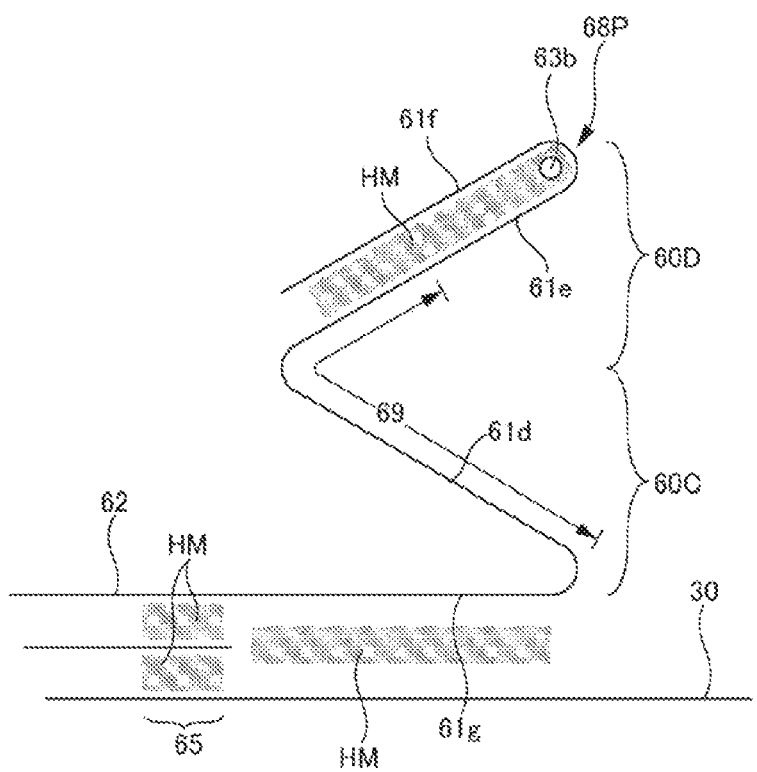

DISPOSABLE WEARING ARTICLE

CROSS-REFERENCE TO RELATED APPLICATIONS

This application is the U.S. national stage application of International Application PCT/JP2019/004809, filed Feb. 12, 2019, which international application was published on Sep. 6, 2019, as International Publication WO 2019/167601 in the Japanese language. The International Application claims priority of Japanese Patent Application No. 2018-034889, filed Feb. 28, 2018. The international application and Japanese application are both incorporated herein by reference, in entirety.

TECHNICAL FIELD

The present invention relates to a disposable wearing article provided with rising gathers on both sides in a width direction.

BACKGROUND ART

Disposable wearing articles such as disposable diapers and sanitary napkins are generally provided with rising gathers that rise from both sides in the width direction of a surface to prevent so-called side leakage. There are various types of rising gathers, but most rising gathers have the following basic structure. That is, rising gathers include a root portion fixed to a disposable wearing article, a main unit section extending from this root portion, a fallen portion formed by fixing a front end portion and a back end portion of the main unit section to a surface of a disposable diaper in a fallen state, a non-fixed rising portion located between the front and fallen portions of the main unit section, and a gather elastic member attached to at least the tip end of the rising portion along the front-back direction.

The rising gathers of a disposable wearing article preferably contact the body surface at a shallower angle, and the rising gathers preferably rise with a narrower width. From this point of view, the rising gather is preferably a folded-up rising gather having a first part extending toward the center in the width direction and a second part extending outward in the width direction from the tip end of the first part.

However, the second part of the folded-up rising gather is a part that rises higher with the first part as a base, and therefore it may fall to the center side in a width direction due to improper wearing or movement of the legs after wearing. In such an improper wearing state, not only the wearing feeling is deteriorated, but also the leakage prevention property is deteriorated. For example, when the parts of the rising gather that are located on both sides of the intergluteal cleft fall in the opposite direction due to inclination toward the intergluteal cleft, that is, the intergluteal cleft side, it is not preferable because the disposable wearing article easily bites into the intergluteal cleft, and a gluteal region is insufficiently covered.

CITATION LIST

Patent Literature

Patent Literature 1: JP 2006-525857 A

SUMMARY OF INVENTION

Technical Problem

Therefore, a main object of the present invention is to provide a folded-back rising gather that is likely to be in an appropriate wearing state at the time of wearing.

Solution to Problem

The various aspects of the disposable wearing article which have solved the above problems will be described below.

<First Aspect>

In a disposable wearing article, in which rising gathers that rise from both sides in the width direction are provided,
  the rising gather has a root portion fixed to a disposable wearing article, a main unit section extending from the root portion, a front fallen portion formed by fixing a front end portion of the main unit section in a fallen state and a back fallen portion formed by fixing a back end portion of the main unit section in a fallen state, and a non-fixed rising portion located between the front fallen portion and the back fallen portion of the main unit section,
  the rising portion has a main region having a first part extending toward the center in a width direction and a second part extending outward in the width direction from a tip end of the first part, in the middle in the front-back direction including a crotch portion, and has a support region composed of a third part extending toward the center in the width direction, between the main region and at least one of the front fallen portion and the back fallen portion,
  the main region has a first gather elastic member attached to at least the tip end of the second part along the front-back direction,
  the support region has a second gather elastic member attached to at least the tip end of the third part along the front-back direction,
  the tip end side of the third part is contracted by the second gather elastic member and is extensible in the front-back direction together with the second gather elastic member, the base edge side of the third part is a non-stretchable portion, and
  the third part has a layer that follows the second part of the main region.

(Function and Effect)

The disposable wearing article has a feature that the shape of the rising portion changes in the front-back direction. That is, the rising portion is a main region having a first part extending toward the center in the width direction and a second part extending outward in the width direction from the tip end of the first part, in the middle in the front-back direction including a crotch portion. Therefore, the basic part of the rising gather comes into contact with the body surface at a shallower angle and rises higher with a narrower width.

In addition, the rising portion of this disposable wearing article has a support regions composed of only the third part extending toward the center in the width direction, between the main region and at least one of the front fallen portion and the back fallen portion. Further, the tip end side of the third part is contracted by a second gather elastic member, and is extensible in the front-back direction together with the second gather elastic member, and the base edge side of the third part is a non-stretchable portion. As a result, the tip end side (width direction center side) of the third part rises up with respect to the base edge side. Here, the third part of the support region has a layer that follows the second part of the main region, such that a force is transmitted in those parts as a continuous part. Therefore, as the tip end side of the third part (width direction center side) rises up with respect to the base edge side, in the portion of the second part of the main region near the support region, the position on the base edge side (width direction center side) is high, and the rising angle is small. As a result, compared to the case without the support region, the rising gather (the main region of the gather) is suitable for wearing, that is, it makes contact with the body surface at a shallower angle and tends to rise higher with a narrow width, and the state is easily maintained.

<Second Aspect>

The disposable wearing article according to the first aspect, in which the third part has a first support portion that follows the first part of the main region, and a second support portion that follows the second part of the main region, and at least the tip end of the second support portion is stacked and integrated with the first support portion.

(Function and Effect)

The sheet that forms the rising gathers does not have to be continuous in the front-back direction, but a continuous sheet is preferable since continuous production in a general production line is possible. In this respect, when configured as in the second aspect, while continuing the sheet from the main region to the support region, the support region can be provided with a third part extending only toward the center in the width direction. Further, the structure of the second aspect is particularly simple. Further, when at least the tip end of the second support portion is stacked and integrated with the first support portion, in the portion of the second part of the main region close to the support region, the base edge side (width direction center side) is located higher than the tip end side, and the rising angle with respect to the width direction becomes negative. As a result, (main regions of) the rising gathers are more likely to be in an appropriate wearing state at the time of wearing, and the wearing state is more easily maintained.

<Third Aspect>

In the disposable wearing article according to the first aspect, the second part of the main region is formed by stacking and integrating a first layer extending outward in a width direction from a tip end of the first part, a second layer extending inward in the width direction from a tip end of the first layer, and a third layer extending outward in the width direction from a tip end of the second layer.

In the support region, a portion that follows the first layer of the main region and a portion that follows the first part of the main region are fixed in a fallen state, the third part has a first support layer that follows the second layer of the main region and a second support layer that follows the third layer of the main region, and at least the tip end of the second support layer is stacked and integrated with the first support layer.

(Function and Effect)

The sheet that forms the rising gathers does not have to be continuous in the front-back direction, but a continuous sheet is preferable since continuous production in a general production line is possible. In this respect, when configured as in the third aspect, while continuing the sheet from the main region to the support region, the support region can be provided with a third part extending only toward the center in the width direction. In particular, although the structure of the third aspect is complicated to some extent, there is an advantage that the number of layers of the third part can be reduced and can be made flexible. Further, when at least the tip end of the second support layer is stacked and integrated with the first support layer, in the portion of the second part of the main region close to the support region, the base edge side (width direction center side) is located higher than the tip end side, and the rising angle with respect to the width direction becomes negative. As a result, (main regions of) the rising gathers are more likely to be in an appropriate wearing state at the time of wearing, and the wearing state is more easily maintained.

<Fourth Aspect>

In a disposable wearing article, in which rising gathers that rise from both sides in the width direction are provided,
  the rising gather includes a root portion fixed to a disposable wearing article, a main unit section extending from the root portion, a front fallen portion formed by fixing a front end portion of the main unit section in a fallen state and a back fallen portion formed by fixing a back end portion of the main unit section in a fallen state, and a non-fixed rising portion located between the front fallen portion and the back fallen portion of the main unit section.

The rising portion has a main region having a first part extending toward the center in a width direction and a second part extending outward in the width direction from a tip end portion of the first part in the middle in the front-back direction including a crotch portion, and has a support region having a third part extending outward in the width direction and a fourth part extending inward in the width direction from a tip end of the third part in a site adjacent to at least one of the front fallen portion and the back fallen portion.

The main region has a first gather elastic member attached to at least the tip end of the first part along the front-back direction.

The support region has a second gather elastic member attached to at least the tip end portion of the fourth part along the front-back direction.

The tip end side of the fourth part is contracted by the second gather elastic member and is extensible in the front-back direction together with the second gather elastic member, a portion from the third part over the base edge side of the fourth part is a non-stretchable portion.

The fourth part has a layer that follows the second part of the main region.

(Function and Effect)

The disposable wearing article also has a feature that the shape of the rising portion changes in the front-back direction. That is, the rising portion is a main region having a first part extending toward the center in the width direction and a second part extending outward in the width direction from the tip end of the first part, in the middle in the front-back direction including a crotch portion. Therefore, the basic part of the rising gather comes into contact with the body surface at a shallower angle and rises higher with a narrower width.

Then, the rising portion of this disposable wearing article has a support region having an outward third part extending outward in the width direction and an inward fourth part extending inward in the width direction from the tip end of the outward first part, between the main region and at least one of the front fallen portion and the back fallen portion. Further, the tip end side of the fourth part is contracted by the second gather elastic member, and it is extensible in the front-back direction together with the second gather elastic member, and a portion from the third part over the base edge side of the fourth part is a non-stretchable portion. As a result, the tip end side (width direction outer side) of the third part rises with respect to the base edge side, and the tip end side (width direction center side) of the fourth part rises with respect to the base edge side with the tip edge side of the third part as a base. Here, the fourth part of the support region has a layer that follows the second part of the main region, such that a force is transmitted in those parts as a continuous part. Therefore, as the tip end side of the fourth part (width direction center side) rises up with respect to the base edge side, in the portion of the second part of the main region near the support region, the position on the base edge side (width direction center side) is high, and the rising angle is small. As a result, compared to the case without the support region, the rising gather (the main region of the gather) is suitable for wearing, that is, it makes contact with the body surface at a shallower angle and tends to rise higher with a narrow width, and the state is easily maintained.

<Fifth Aspect>

In the disposable wearing article according to the fourth aspect,
- the second part of the main region is formed by stacking and integrating a first layer extending outward in the width direction from a tip end of the first part, a second layer extending inward in the width direction from a tip end of the first layer, and a third layer extending outward in the width direction from a tip end of the second layer,
- in the support region, a portion that follows the first part of the main region is fixed in a fallen state,
- the fourth part has a first support layer of that follows the second layer of the main region and a second support layer that follows the third layer of the main region, and at least the tip end of the second support layer is stacked and integrated with the first support layer,
- the third part is formed by a third support layer that follows the first layer of the main region, and the first support layer and the third support layer are not bonded.

(Function and Effect)

The sheet that forms the rising gathers does not have to be continuous in the front-back direction, but a continuous sheet is preferable since continuous production in a general production line is possible. In this respect, when configured as in the fifth aspect, while continuing the sheet from the main region to the support region, the support region can be provided with the third part and the fourth part of the fourth aspect. Further, when at least the tip end of the second support layer is stacked and integrated with the first support layer, in the portion of the second part of the main region close to the support region, the base edge side (width direction center side) is located higher than the tip end side, and the rising angle with respect to the width direction becomes negative. As a result, (main regions of) the rising gathers are more likely to be in an appropriate wearing state at the time of wearing, and the wearing state is more easily maintained.

<Sixth Aspect>

In the disposable wearing article according to any one of the first to fifth aspects, which is an underpants-type disposable wearing article,
- a front outer member forming at least a lower torso portion of a front body and a back outer member forming at least a lower torso portion of a back body are separately provided, the front outer member and the back outer member are separated in a front-back direction,
- an inner member containing an absorber extends in the front-back direction from the front outer member to the back outer member, and is bonded to the front outer member and the back outer member, respectively,
- a side seal portion in which both side portions of the front outer member and both side portions of the back outer member are bonded, a waist opening and a pair of left and right leg openings are provided,
- the inner member has rising gathers that rise from both sides, and
- the main region is continuous from the front outer member to the back outer member.

(Function and Effect)

In underpants-type disposable wearing articles such as underpants-type disposable diapers, the maximum width of the inner member is designed according to the crotch width of the wearer, and the rising gathers rise from both sides of the inner member, and therefore the width of the rising gather is close to the crotch width. For this reason, underpants-type disposable diapers are more likely to be in an improper wearing state, such as rising gathers falling to the center side in the width direction on the front surface side and the back surface side of the crotch portion. In particular, in outer two-piece type underpants-type disposable diapers in which a front outer member and a back outer member are separately provided and are separated in a front-back direction, the rising gathers are likely to be in an improper wearing state since the portion not supported by the front outer member and the back outer member is long in the front-back direction.

On the other hand, in the present aspect, by providing the rising gather having the above-described support region, the rising gather is unlikely to be in an improper wearing state. Further, it is obvious that the main region is continuous from the front outer member to the back outer member, such that the side leakage prevention effect is excellent.

Advantageous Effects of Invention

As described above, according to the present invention, there are advantages such as a disposable wearing article provided with rising gathers that are likely to be in a proper wearing state at the time of wearing.

BRIEF DESCRIPTION OF DRAWINGS

FIG. 1 is a plan view illustrating the inner surface of an underpants-type disposable diaper in a spread state.

FIG. 2 is a plan view illustrating the outer surface of an underpants-type disposable diaper in a spread state.

FIG. 3 is a cross-sectional view taken along line 2-2 in FIG. 1.

FIG. 4 is a cross-sectional view taken along line 3-3 in FIG. 1.

FIG. 5(a) is a cross-sectional view taken along line 4-4 in FIG. 1. FIG. 5(b) is a cross-sectional view taken along line 5-5 in FIG. 1.

FIG. 6 is a perspective view of an underpants-type disposable diaper.

FIG. 7 is a plan view illustrating a main part of an underpants-type disposable diaper.

FIG. 8 is a plan view illustrating a back side main part of an underpants-type disposable diaper in a spread state.

FIG. 9(a) is a cross-sectional view taken along line 6-6 in FIG. 8. FIG. 9(b) is a cross-sectional view taken along line 7-7 in FIG. 8.

FIG. 10 is a cross-sectional view taken along line 8-8 in FIG. 8.

FIG. 14(a) is an enlarged cross-sectional view of a main part of a main region, and FIG. 14(b) is an enlarged cross-sectional view of a main part of a support region, in another example.

FIG. 15 is a cross-sectional view passing through a support region in another example.

FIG. 16 is a cross-sectional view illustrating an enlarged main part of a support region in another example.

DESCRIPTION OF EMBODIMENTS

Figure 11:
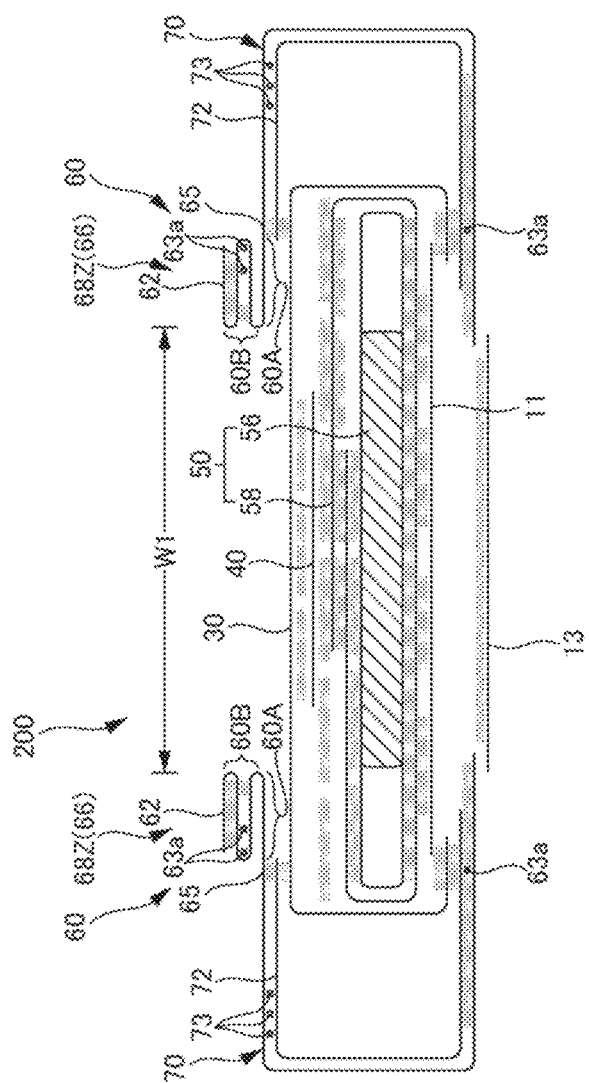
FIG. 11 is a cross-sectional view passing through a main region in another example.

Hereinafter, embodiments of the present invention will be described in detail with reference to the accompanying drawings. The dotted pattern portion in the cross sectional view indicates an adhesive as a bonding means for bonding respective constituent members positioned on the front surface side and the back surface side thereof. The application of a hot melt adhesive is performed by the solid coating, bead coating, curtain coating, summit coating, spiral coating, or pattern coating (transfer of the hot melt adhesive in a letterpress method) of a hot melt adhesive. Alternatively, in the fixed portion of the elastic member, the adhesive is applied to the outer peripheral surface of the elastic member by using a comb gun, a sure wrap coating or the like in place of or in addition to the above. Examples of the hot melt adhesive include, but are not limited to, adhesives of the EVA type, adhesive rubber type (elastomer), polyolefin-based, and polyester/polyamide-based. As a bonding means for bonding respective constituent members, a means by material welding such as heat sealing or ultrasonic sealing can also be used.

FIGS. 1 to 10 illustrate an example of an underpants-type disposable diaper. This underpants-type disposable diaper is provided with a front outer member 12F forming at least a lower torso portion of a front body F and a back outer member 12B forming at least a lower torso portion of a back body B, and an inner member 200 provided inside the outer members 12F and 12B so as to extend from the front outer member 12F to the back outer member 12B through a crotch portion. Both sides of the front outer member 12F and both sides of the back outer member 12B are bonded to form a side seal portion 12A. Thus, an opening formed by the front and back end portions of the outer members 12F and 12B becomes a waist opening WO through which the torso of a wearer passes. Portions surrounded by the lower edges of the outer members 12F and 12B and the side edges of the inner member 200 on both sides in the width direction of the inner member 200 serve as leg openings LO through which the legs pass. The inner member 200 is a portion to absorb and hold excrement such as urine, and the outer members 12F and 12B are portions for supporting the inner member 200 with respect to the wearer's body. The reference character Y denotes the maximum length of a diaper in a spread state (the length in the front-back direction from the edge of the waist opening WO of the front body F to the edge of the waist opening WO of the back body B), and the reference character X denotes the maximum width of a diaper in a spread state.

An underpants-type disposable diaper according to the present embodiment has a lower torso region T defined as a front-back direction range (a range in the front-back direction from the waist opening WO to the upper end of the leg opening LO) having the side seal portion 12A and an intermediate region L defined as a front-back direction range of a portion forming the leg opening LO (between the region in the front-back direction having the side seal portion 12A of the front body F and the region in the front-back direction having the side seal portion 12A of the back body B). The lower torso region T can be divided into a "waist portion" W which conceptually forms an edge portion of the waist opening and an "under-waist portion" U which is a portion lower than the waist portion W. Normally, in the case of having a boundary where stretching stress of the width direction WD changes in the lower torso region T (for example, the fineness and stretch rate of the elastic member change), the waist opening WO side of the boundary in the lower torso region T is the waist portion W. When there is no such boundary, the waist opening WO side of the absorber 56 or the inner member 200 is the waist portion W. The length in the front-back direction varies depending on the size of a product and can be appropriately determined. For example, the waist portion W can be set to 15 to 40 mm, and the under-waist portion U can be set to 65 to 120 mm. On the other hand, both side edges of the intermediate region L narrow in a U shape or a curved shape along the periphery of the legs of a wearer, and this is a site along the periphery of the wearer's legs.

(Outer Member)

The outer members 12F and 12B are not an integral outer member that extends from the front body F to the back body B through the crotch, and correspond to a front outer member 12F that is a portion that forms at least the lower torso portion of the front body F and a back outer member 12B that is a portion that forms at least the lower torso portion of the back body B. The front outer member 12F and the back outer member 12B are not continuous on the crotch side and are separated in the front-back direction LD. The separation distance 12d can be set to, for example, about 150 to 250 mm.

The outer members 12F and 12B have a lower torso portion which is a front-back direction range corresponding to the lower torso region T. Further, in the present embodiment, the back outer member 12B has a longer dimension in the front-back direction than the front outer member 12F, and the front outer member 12F does not have a portion corresponding to the intermediate region L, but the back outer member 12B has a gluteal cover portion C extending from the lower torso region T to the intermediate region L side. Although not illustrated, the front outer member 12F is also provided with an inguinal cover portion extending from the lower torso region T to the intermediate region L side, or although the inguinal cover portion is provided, a gluteal cover portion is not provided. Further, it is not necessary to provide portions corresponding to the intermediate region L on both the front outer member 12F and the back outer member 12B. In the illustrated embodiment, the lower edge of the gluteal cover portion C is formed in a straight line along the width direction WD similarly to the lower edge of the front outer member 12F. However, the lower edge of the gluteal cover portion C may be a curve so as to be positioned on the waist opening side on the outside in the width direction.

The front-back direction dimension of the side edge of the gluteal cover portion C may be appropriately determined, but if the length is excessively long, the corners of the side edges on the leg opening LO side may flutter, and the appearance and wearing feeling may be deteriorated. Therefore, the length is preferably 20 mm or less.

As illustrated in FIGS. 4 and 5, in the outer members 12F and 12B, the outer sheet layer 12S and the inner sheet layer 12H located on the outer side and the inner side of the elastic members 15 to 19 to be described later are bonded by a bonding means, such as hot melt adhesive or welding. The sheet material forming the outer sheet layer 12S and the sheet material forming the inner sheet layer 12H may be a common sheet material or may be individual sheet materials. That is, in the former case, in part or the whole of the outer member, the inner sheet layer 12H and the outer sheet layer 12S are respectively formed by the inner portion and the outer portion of one sheet material folded back at the edge of the waist opening WO (which may be the leg opening side edge). Incidentally, in the former form, there is an advantage that the number of materials of the sheet material is small, and in the latter form, there is an advantage that positional deviation is hard to occur when the inner sheet layer 12H and the outer sheet layer 12S are bonded together. The illustrated embodiment corresponds to the latter, and although the sheet material forming the inner sheet layer 12H extends only up to the edge of the waist opening WO, the sheet material forming the outer sheet layer 12S wraps around the waist side edge of the sheet material of the inner sheet layer 12H and is folded back inward. Further, this folded-back portion is a cover sheet layer 12r extending over the entire width direction of the outer member to a position where overlaps with the end of the inner member 200 on the waist opening WO side. The cover sheet layer 12r may be formed by attaching a dedicated sheet material to the inside of the inner sheet layer 12H without forming the sheet material of the outer sheet layer 12S by folding it back.

The sheet material used for the outer sheet layer 12S and the inner sheet layer 12H can be used without particular limitation, but a nonwoven fabric is preferable, and examples of the nonwoven fabric include synthetic fibers such as polyolefin-based such as polyethylene and polypropylene, polyester-based, polyamide-based, and the like, and mixed fibers and composite fibers in which two or more of these are used. Further, the nonwoven fabric may be manufactured by any processing. Examples of the processing method include known methods such as a spun lace method, a spun bond method, a thermal bond method, a meltblown method, a needle punch method, an air-through method, and a point bond method. When a nonwoven fabric is used, its basis weight is preferably about 10 to 30 g/m$^2$.

(Stretchable Region/Non-Stretchable Region)

The outer members 12F and 12B are provided with elastic members 15 to 19 between the outer sheet layer 12S and the inner sheet layer 12H in order to enhance fitting to the wearer's waist, and a stretchable region A2 which elastically expands and contracts in the width direction WD is formed accompanying expansion and contraction of the elastic member. In this stretchable region A2, the outer sheet layer 12S and the inner sheet layer 12H contract as the elastic member contracts in a natural length state, and wrinkles or pleats are formed. When the stretchable region elongates in the longitudinal direction of the elastic member, the outer sheet layer 12S and the inner sheet layer 12H can be elongated to a predetermined stretch rate at which the outer sheet layer 12S and the inner sheet layer 12H elongate without wrinkles. As the elastic members 15 to 19, known elastic members such as a belt-shaped elastic member, a net-shaped elastic member, and a film-shaped elastic member can be used without particular limitation, in addition to the elongated elastic member (illustrated example) such as a rubber thread. As the elastic members 15 to 19, synthetic rubber may be used, and also natural rubber may be used.

For bonding the outer sheet layer 12S and the inner sheet layer 12H in the outer members 12F and 12B and fixing the elastic members 15 to 19 sandwiched therebetween, at least one of hot melt adhesives by various application methods and a fixing means by material welding such as a heat sealing, ultrasonic sealing and the like can be used. It is preferable that the portions other than the adhesive portions of the elastic members 15 to 19 are not adhered or are weakly adhered in order to deteriorate flexibility when the entire surfaces of the outer members 12F and 12B are tightly fixed. In the illustrated embodiment, by applying a hot melt adhesive only to the outer peripheral surfaces of the elastic members 15 to 19 by an application means such as a comb gun or a sure wrap nozzle and sandwiching them between both sheet layers 12S and 12H, fixing of the elastic members 15 to 19 to the both sheet layers 12S and 12H and fixing between the both sheet layers 12S and 12H are performed only by the hot melt adhesive applied to the outer peripheral surfaces of the elastic members 15 to 19. The elastic members 15 to 19 can be fixed to the outer sheet layer 12S and the inner sheet layer 12H only at both ends in the extending direction in the stretchable region.

When the elastic members 15 to 19 in the illustrated embodiment is described in detail, between the outer sheet layer 12S and the inner sheet layer 12H in the waist portion W of the outer members 12F and 12B, a plurality of waist portion elastic members 17 is attached at intervals in the front-back direction so as to be continuously extend over the width direction WD. One or a plurality of waist portion elastic members 17 disposed in a region adjacent to the under-waist portion U may overlap with the inner member 200 or may be provided on both sides in the width direction except for the central portion in the width direction overlapping with the inner member 200. As this waist portion elastic members 17, about 3 to 22 rubber threads having a fineness of 155 to 1880 dtex, particularly about 470 to 1240 dtex (in the case of synthetic rubber) (in the case of natural rubber, a cross section area of about 0.05 to 1.5 mm$^2$, particularly about 0.1 to 1.0 mm$^2$) are preferably provided at an interval of 4 to 12 mm, such that a stretch rate of the width direction WD of the waist portion W is preferably about 150 to 400%, particularly about 220 to 320%. Further, it is not necessary to use the waist portion elastic member 17 having the same thickness or to set the same stretch rate in the entire front-back direction LD of the waist portion W. For example, at the upper portion and the lower portion of the waist portion W, the fineness and the stretch rate of the elastic member 17 may be different.

In addition, between the outer sheet layer 12S and the inner sheet layer 12H in the under-waist portion U of the outer members 12F and 12B, a plurality of elastic members of the under-waist portions 15 and 19 composed of elongated elastic members are attached at intervals in the front-back direction.

As the elastic member of the under-waist portions 15 and 19, about 5 to 30 rubber threads having a fineness of 155 to 1880 dtex, particularly about 470 to 1240 dtex (in the case of synthetic rubber) (in the case of natural rubber, a cross section area of about 0.05 to 1.5 mm$^2$, particularly about 0.1 to 1.0 mm$^2$) are preferably provided at an interval of 1 to 15 mm, particularly 3 to 8 mm, such that a stretch rate of the width direction WD of the under-waist portion U is preferably about 200 to 350%, particularly about 240 to 300%.

Further, between the outer sheet layer 12S and the inner sheet layer 12H in the gluteal cover portion C of the back outer member 12B, an elastic member of the cover portion 16 composed of the elongated elastic member is attached.

As the elastic member of the cover portion 16, one or a plurality of rubber threads having a fineness of 155 to 1880 dtex, particularly about 470 to 1240 dtex (in the case of synthetic rubber) (in the case of natural rubber, a cross section area of about 0.05 to 1.5 mm², particularly about 0.1 to 1.0 mm²) are preferably provided at intervals in the front-back direction, such that a stretch rate of the width direction WD of the gluteal cover portion C is preferably about 150 to 400%, particularly about 180 to 260%.

Similarly, in the case where an inguinal cover portion is provided on the front outer member 12F, it is possible to provide the elastic member of the cover portion.

When the elastic members 15, 16, and 19 are provided in the front-back direction range having the absorber 56 like the under-waist portion U and the gluteal cover portion C in the illustrated embodiment, to prevent contraction of the absorber 56 in the width direction WD in part or the whole of the range, the intermediate portion in the width direction (preferably including the entire inner and outer joined portions 201 and 202) including a part or the whole of the portion overlapping with the absorber 56 in the width direction WD is a non-stretchable region A1, and both sides in the width direction is a stretchable region A2. It is preferable that the waist portion W is formed as the stretchable region A2 over the entire width direction WD. However, similarly to the under-waist portion U, the non-stretchable region A1 may be provided in the middle in the width direction.

The stretchable region A2 and the non-stretchable region A1 as described above is constructed by supplying the elastic members 15 to 17 and 19 between the inner sheet layer 12H and the outer sheet layer 12S, fixing the elastic members 15, 16, and 19 in the stretchable region A2 at least at the both ends in the extending direction via a hot melt adhesive, not fixing in the region to be the non-stretchable region A1, and cutting the elastic members 15, 16, and 19 by pressing and heating at one place in the middle of the width direction or finely cutting almost all of the elastic members 15, 16, 19 by pressing and heating, such that the elasticity is remained in the stretchable region A2 while suppressing the elasticity in the non-stretchable region A1. In the former case, as illustrated in FIG. 4, in the non-stretchable region A1, a cutting remainder continuing from the elastic members 15, 16, and 19 of the stretchable region A2 is remained between the outer sheet layer 12S and the inner sheet layer 12H in a state individually contracting to a natural length as an ideal elastic member 18. In the latter case, although not illustrated, the cutting remainder continuing from the elastic members 15, 16, and 19 of the stretchable region A2 and cut pieces of the elastic members not continuous with the elastic members 15, 16, and 19 of the stretchable region A2 are remained between the outer sheet layer 12S and the inner sheet layer 12H in a state of individually contracting to a natural length as an ideal elastic member.

(Cover Nonwoven Fabric)

In outer two-piece type underpants-type disposable diapers, since the inner member 200 is exposed between the front outer member 12F and the back outer member 12B, in order to prevent the liquid impervious sheet 11 from being exposed on the back surface of the inner member 200, it is preferable that the cover nonwoven fabric 13 that covers the back surface of the inner member 200 from a space between the front outer member 12F and the inner member 200 to a space between the back outer member 12B and the inner member 200 be provided.

The nonwoven fabric used for the cover nonwoven fabric 13 is not particularly limited depending on the type of fibers and the method of fiber binding (entanglement), and for example, the same materials as those of the outer members 12F and 12B can be appropriately selected. However, it is desirable to use an air-through nonwoven fabric, and, in such case, the basis weight is preferably 20 to 40 g/m², and the thickness is preferably 0.3 to 1.0 mm. As the cover nonwoven fabric 13, an imperforate nonwoven fabric having no holes penetrating the front and back may be used, or a perforated nonwoven fabric having a large number of holes penetrating the front and back at intervals may be used.

The range of the cover nonwoven fabric 13 in the front-back direction is not particularly limited, and as illustrated in FIG. 5, the range may extend in the front-back direction LD over entirely from the front end to the back end of the inner member 200, or as illustrated in FIG. 7, the range may extend in the front-back direction LD from the intermediate position in the front-back direction of the region where the front outer member 12F and the inner member 200 overlap to the intermediate position in the front-back direction of the region where the back outer member 12B and the inner member 200 overlap. In the case of the example illustrated in FIG. 7, a length 13y in the front-back direction of the overlapping portion of the cover nonwoven fabric 13 and the front outer member 12F and a length 13y in the front-back direction of the overlapping portion of the cover nonwoven fabric 13 and the back outer member 12B can be appropriately determined, but in the usual case, the length 13y can be set to about 20 to 40 mm each.

A range in the width direction of the cover nonwoven fabric 13 is a range within which the back side exposed portion of the liquid impervious sheet 11 can be concealed. Therefore, in the illustrated example, since the liquid impervious sheet 11 is exposed between the base edge of the right and left rising gathers 60, the cover nonwoven fabric 13 is provided so as to cover a range in the width direction from a back surface side of the base portion of at least one of the rising gathers 60 to the back surface side of the base portion of the other rising gather 60. As a result, the liquid impervious sheet 11 can be covered with the cover nonwoven fabric 13 and the gather sheet 62 of the rising gather 60. Further, even if the both ends in the width direction of the cover nonwoven fabric 13 do not cover the back surface side of the base portion of the rising gather 60, and the gather sheet 62 covers the both ends in the width direction of the cover nonwoven fabric 13, the liquid impervious sheet 11 can be covered with the cover nonwoven fabric 13 and the gather sheet 62.

The inner surface and the outer surface of the cover nonwoven fabric 13 can be adhered to the opposite surfaces via a hot melt adhesive. The fixing region of the cover nonwoven fabric 13 covers the entire front-back direction and the entire width direction of the cover nonwoven fabric 13, or a part thereof may be non-fixed. For example, if both ends in the width direction of the cover nonwoven fabric 13 are not fixed, even if the side portion of the absorber 56 is somewhat contracted due to the influence of the rising gathers 60, it is less likely to be affected thereby, and there is an advantage that wrinkles and folds are hardly formed on the cover nonwoven fabric 13. In this case, the width of the non-fixed portion at both ends in the width direction of the cover nonwoven fabric 13 may be suitably determined, but it may be, for example, 3 to 10 mm, preferably 5 to 8 mm.

(Inner and Outer Joined Portion)

The inner member 200 can be fixed to the outer members 12F and 12B by a bonding means by material welding such as heat sealing or ultrasonic sealing or a hot melt adhesive. In the illustrated example, the inner member 200 is fixed to the inner surface of the outer members 12F and 12B via a hot melt adhesive applied to the back surface of the inner member 200, that is, in this case, the back surface of the liquid impervious sheet 11 and the root portion 65 of the rising gather 60. Inner and outer joined portions 201 and 202 for fixing the inner member 200 and the outer members 12F and 12B can be provided almost entirely in a region where those are overlapped with each other, as illustrated in FIG. 2, and, for example, they can be provided in portions excluding both ends in the width direction of the inner member 200.

(Inner Member)

The inner member 200 can have an arbitrary shape, but in the illustrated form, it is rectangular. As illustrated in FIGS. 1 to 5, the inner member 200 includes an absorbent element 50, a top sheet 30 that covers the front surface side (body side) of the absorbent element 50, and a liquid impervious sheet 11 that covers the back surface side of the absorbent element 50, and plays a role of absorbent and holding functions. The reference character 40 denotes an intermediate sheet (second sheet) provided between the top sheet 30 and the absorbent element 50 in order to promptly transfer liquid having permeated through the top sheet 30 to the absorbent element 50. The reference character 60 denotes the rising gather 60 extending from both sides of the inner member 200 so as to be in contact with a leg portion of a wearer in order to prevent excrement from leaking to both sides of the inner member 200.

(Absorbent Element)

The absorbent element 50 has the absorber 56 and a package sheet 58 packaging the entire absorber 56. The package sheet 58 can also be omitted.

(Absorber)

The absorber 56 can be formed of an assembly of fibers. As this fiber assembly, besides those obtained by accumulating short fibers such as fluff pulp and synthetic fibers, a filament assembly obtained by opening tows (fiber bundles) of synthetic fibers such as cellulose acetate as required can also be used. When fluff pulp or short fibers are accumulated, fiber basis weight can be set to, for example, about 100 to 300 g/m$^2$, and in the case of a filament assembly, fiber basis weight can be set to about 30 to 120 g/m$^2$. In the case of a synthetic fiber, the fineness is, for example, 1 to 16 dtex, preferably 1 to 10 dtex, more preferably 1 to 5 dtex. In the case of filament assembly, the filaments may be non-crimped fibers, but are preferably crimped fibers. The degree of crimp of the crimped fiber can be, for example, about 5 to 75 crimps, preferably 10 to 50 crimps, and more preferably about 15 to 50 crimps per 2.54 cm. In addition, crimped fibers which are uniformly crimped can be used. It is preferable to disperse and hold the super absorbent polymer particles in the absorber 56.

The absorber 56 may have a rectangular shape, and, as illustrated in FIG. 7, etc., preferably has an hourglass shape having a narrowing portion 56N with a width narrower than both front and back sides in the middle in the front-back direction, since the fitting of the absorber 56 itself and the rising gather 60 around the legs is improved.

The dimension of the absorber 56 can be appropriately determined as far as it includes a crotch portion, but it is preferable that it extends to the peripheral edges of the inner member 200 or the vicinity thereof in the front-back direction LD and the width direction WD. The reference character 56X denotes the maximum width of the absorber 56.

(Super Absorbent Polymer Particle)

The absorber 56 can contain super absorbent polymer particles partially or entirely. The super absorbent polymer particle means "powder" in addition to "particle". The super absorbent polymer particles 54 used for this type of disposable diapers can be used as they are, and it is desirable that the proportion of particles remaining on a sieve is less than 30% by weight by sieving (shaking for 5 minutes) using, for example, a standard sieve of 500 μm (JIS Z 8801-1: 2006). In addition, it is desirable that the proportion of particles remaining on the sieve by sieving (shaking for 5 minutes) using a standard sieve of 180 μm (JIS Z 8801-1: 2006) be 60% by weight or more.

The material of the super absorbent polymer particles is not particularly limited, but materials having a water absorption capacity of 40 g/g or more are suitable. Examples of the super absorbent polymer particles include starch-based, cellulose-based, and synthetic polymer-based particles, and starch-acrylic acid (salt) graft copolymers, saponified starch-acrylonitrile copolymers, crosslinked sodium carboxymethylcellulose, and acrylic acid (salt) polymers can be used. As the shape of the super absorbent polymer particles, particulate materials which are usually used are preferable, but other shapes can also be used.

The super absorbent polymer particles having a water absorption rate of 70 seconds or less, particularly 40 seconds or less, are suitably used. If the water absorption rate is too slow, back-flow, in which the liquid fed into the absorber 56 returns to the outside of the absorber 56, is likely to occur.

As the super absorbent polymer particles, those having a gel strength of 1,000 Pa or more are preferably used. Thereby, even when the absorber 56 is bulky, it is possible to effectively suppress stickiness after liquid absorption.

The basis weight of the super absorbent polymer particles can be appropriately determined according to the absorption amount required for the use of the absorber 56. Therefore, although it cannot be said unconditionally, the basis weight can be 50 to 350 g/m$^2$. When the basis weight of the polymer is less than 50 g/m$^2$, it is difficult to ensure the absorption amount. When it exceeds 350 g/m$^2$, the effect is saturated.

If necessary, the content of the super absorbent polymer particles can be adjusted in the planar direction of the absorber 56. For example, it is possible to increase the content in an excretory site of liquid compared to the other sites. Further, a portion without super absorbent polymer particle can be provided locally (for example, in a spot shape) in the planar direction of the absorber 56.

(Package Sheet)

When the package sheet 58 is used, tissue paper, particularly crepe paper, a nonwoven fabric, a poly lamina nonwoven fabric, a sheet with small openings can be used as the material. However, it is desirable that the sheet from which the super absorbent polymer particles do not come off is used. When a nonwoven fabric is used in place of crepe paper, a hydrophilic SMS nonwoven fabric (SMS, SSMMS, etc.) is particularly suitable, and polypropylene, polyethylene/polypropylene composite material and the like can be used as the material. The basis weight is desirably 5 to 40 g/m$^2$, particularly desirably 10 to 30 g/m$^2$.

The wrapping mode of the package sheet 58 can be appropriately determined. However, from the viewpoints of ease of manufacturing and prevention of leakage of super absorbent polymer particles from the front and back end edges, it is preferable that the package sheet 58 is wound around in a cylindrical shape so as to surround the front and back surfaces and both side surfaces of the absorber 56, the front and back edge portions are protruded from the front and back of the absorber 56, and the overlapping portion and the overlapping portion of the front-back protruding portions are bonded by bonding means such as hot melt adhesive, material welding, or the like.

(Top Sheet)

The top sheet 30 has a property of permeating liquid, and examples of the top sheet 30 include a perforated or imperforate nonwoven fabric and a porous plastic sheet. Among them, a raw fiber of the nonwoven fabric is not particularly limited. Examples of the raw fiber include synthetic fibers such as polyolefin-based such as polyethylene and polypropylene, polyester-based, and polyamide-based, regenerated fibers such as rayon and cupra, natural fibers such as cotton, and mixed fibers and composite fibers in which two or more of these are used. Further, the nonwoven fabric may be manufactured by any processing. Examples of the processing method include known methods such as a spun lace method, a spun bond method, a thermal bond method, a meltblown method, a needle punch method, an air-through method, and a point bond method. For example, if flexibility and drapeability are required, the spunbond method and the spun lace method are preferable processing methods, and if bulkiness and softness are required, the air-through method, the point bond method, and the thermal bond method are preferable processing methods.

Further, the top sheet 30 may be made of one sheet or a laminated sheet obtained by bonding two or more sheets. Similarly, the top sheet 30 may be composed of one sheet or two or more sheets with respect to the plane direction.

Both sides of the top sheet 30 may be folded back to the back surface side at the side edge of the absorbent element 50 or protruded laterally beyond the side edge of the absorbent element 50 without folding back.

For the purpose of preventing positional deviation with respect to the member on the back surface side, it is desirable that the top sheet 30 be fixed to a member adjacent to the back surface side by a bonding means by material welding such as heat sealing or ultrasonic sealing or a hot melt adhesive. In the illustrated example, the top sheet 30 is fixed to the surface of the intermediate sheet 40 and the surface of the package sheet 58, which is located on the front surface side of the absorber 56, by a hot melt adhesive applied on the back surface thereof.

(Intermediate Sheet)

To quickly transfer liquid having permeated through the top sheet 30 to the absorber, it is possible to provide an intermediate sheet (also referred to as a "second sheet") 40 having a higher liquid permeation rate than the top sheet 30. This intermediate sheet 40 is intended to quickly transfer the liquid to the absorber to improve the absorption performance of the absorber and prevent the "returning" phenomenon of the absorbed liquid from the absorber. The intermediate sheet 40 can also be omitted.

Examples of the intermediate sheet 40 include the same material as the top sheet 30, a spun lace nonwoven fabric, a spunbond nonwoven fabric, SMS nonwoven fabric, a pulp nonwoven fabric, a mixed sheet of pulp and rayon, a point bond nonwoven fabric, or a crepe paper. In particular, an air-through nonwoven fabric is preferable because it is bulky. It is preferable to use a composite fiber having a core-sheath structure for the air-through nonwoven fabric. In this case, resin used for the core may be polypropylene (PP), but polyester (PET) having high rigidity is preferable. The basis weight is preferably 17 to 80 g/m$^2$, more preferably 25 to 60 g/m$^2$. The fineness of the raw fiber of the nonwoven fabric is preferably 2.0 to 10 dtex. To increase the bulkiness of the nonwoven fabric, it is also preferable to use eccentric fibers, hollow fibers, eccentric and hollow fibers, whose core is not in the center, as mixed fibers of all or a part of the raw material fibers.

Although the intermediate sheet 40 in the illustrated example is shorter than the width of the absorber 56 and disposed at the center, it may be provided throughout the maximum width. The length of the intermediate sheet 40 in the front-back direction may be the same as the maximum length of a diaper, may be the same as the length of the absorbent element 50, or may be within a short length range around a region receiving a liquid.

For the purpose of preventing positional deviation with respect to the member on the back surface side, it is desirable that the intermediate sheet 40 be fixed to a member adjacent to the back surface side by a bonding means by material welding such as heat sealing or ultrasonic sealing or a hot melt adhesive. In the illustrated example, the intermediate sheet 40 is fixed to the surface of the package sheet 58, which is located on the front surface side of the absorber 56, by a hot melt adhesive applied on the back surface thereof.

(Liquid Impervious Sheet)

The material of the liquid impervious sheet 11 is not particularly limited, but examples of the material include a plastic film made of a polyolefin-based resin such as polyethylene and polypropylene, a laminated nonwoven fabric having a plastic film on the surface of a nonwoven fabric, and a laminated sheet obtained by bonding nonwoven fabrics or the like on a plastic film. In the liquid impervious sheet 11, it is preferable to use a material having liquid impermeability and moisture permeability that has been favorably used from the viewpoint of prevention of stuffiness. As the moisture-permeable plastic film, a microporous plastic film is widely used. The microporous plastic film is obtained by stretching a sheet in a monoaxial or biaxial direction after forming the sheet by kneading an inorganic filler in a polyolefin-based resin such as polyethylene or polypropylene. In addition to this, a nonwoven fabric using a micro-denier fiber and a liquid impervious sheet in which a plastic film is not used by increasing leakage resistance by reducing gaps of fiber by applying heat and pressure and by coating with super absorbent polymer, a hydrophobic resin, or a water repellent agent can also be used as the liquid impervious sheet 11. However, it is desirable to use a resin film to obtain sufficient adhesive strength in the case of adhering to the cover nonwoven fabric 13 to be described later via a hot melt adhesive.

The liquid impervious sheet 11 may have a width that fits on the back surface side of the absorbent element 50 as illustrated in the drawing. Alternatively, to enhance leakage resistance, the liquid impervious sheet 11 can also be disposed around the both sides of the absorbent element 50 to extend to the both sides of the side surface of the top sheet 30 of the absorbent element 50. It is appropriate that the width of this extending portion is about 5 to 20 mm on each side.

(Rising Gather)

The rising gather 60 has a rising portion 68 that rises from the side portion of the inner member 200, and the rising portion 68 is in contact with the range from the wearer's groin region to the gluteal region through the leg portion to prevent side leakage.

The rising gather of the illustrated example has a two-layered structure in which a belt shaped gather sheet 62 having a length equal to the length in the front-back direction of the inner member 200 is folded back in the width direction WD at a portion to be a tip portion to form a two-layer structure, and a plurality of elongated gather elastic members 63a and 63b is fixed with intervals in the width direction WD in a stretched state along the longitudinal direction between layers. A base portion (an end portion on the side opposite to the sheet folded-back portion in the width direction WD) positioned on the opposite side of the tip portion of the rising gathers 60 is the root portion 65 fixed to the side portion on the back surface side of the liquid impervious sheet 11 in the inner member 200, and portions other than the root portion 65 are a main unit section 66 extending from the root portion 65. Further, the front end portion and the back end portion of the main unit section 66 are a front fallen portion 67F and a back fallen portion 67B which are fixed in a fallen state. On the other hand, the front-back direction intermediate portion located between the front fallen portion 67F and the back fallen portion 67B is an unfixed rising portion 68, and the gather elastic members 63a and 63b is fixed to at least the tip end portion of the rising portion 68 along the front-back direction LD in a stretched state.

Characteristically, as illustrated in FIGS. 3, 4, 8(a), and 9, the shape of the rising portion 68 changes in the front-back direction LD. Specifically, as illustrated in FIGS. 3, 8(a), and 9(a), the rising portion 68 has a main region 68Z including a first part 60A extending toward the center in the width direction and a second part 60B extending outward in the width direction from the tip of the first part 60A, in the middle of the front-back direction LD including the crotch portion. The main region 68Z has a first gather elastic member 63a attached to at least the tip end of the second part 60B along the front-back direction LD. Further, as illustrated in FIGS. 4, 8(a), and 9(b), the rising portion 68 has a support region 68P formed only of a third part 60C extending toward the center in the width direction between the main region 68Z and the back fallen portion 67B. The support region 68P has a second gather elastic member 63b attached to at least the tip end of the third part along the front-back direction LD. Further, the tip end side of the third part 60C is contracted by the second gather elastic member 63b, and it is extensible in the front-back direction LD together with the second gather elastic member 63b. The base edge side of the third part 60C is a non-stretchable portion 69, and the third part 60C has a layer that follows the second part 60B of the main region.

As illustrated in FIG. 8, it is preferable that the main region 68Z is continuous from the front outer member 12F to the back outer member 12B since the side leakage prevention effect is excellent. In this case, the support region 68P is arranged in a region overlapping with the back outer member 12B. In particular, the main region 68Z is preferably continuous from a position overlapping with at least one elastic member 19 in the front outer member 12F to a position overlapping with at least one elastic member 16, 19 in the back outer member 12B.

The number of gather elastic members 63a and 63b is preferably 2 to 6, and more preferably 3 to 5. An appropriate arrangement interval 60d is 3 to 10 mm. With such a configuration, a range in which the gather elastic members 63a and 63b are disposed easily comes into surface contact with the skin. Further, the first gather elastic member 63a can be arranged not only in the second part 60B but also in the first part 60A. On the other hand, the second gather elastic member 63b may be arranged at a portion other than the tip end portion of the third part 60C. From this viewpoint, the number of the second gather elastic members 63b is preferably one or two, and is preferably provided at a position near the tip end of the third part 60C. Further, the second gather elastic member 63b may be the same elastic member that is continuous with the first gather elastic member 63a, or may be another elastic member. It is desirable that a contraction force of the gather elastic members 63a and 63b does not act on the front fallen portion 67F and the back fallen portion 67B, like the non-stretchable portion 69. Note that, the part where the contraction force of these gather elastic members 63a and 63b does not act includes, in addition to the parts that do not have the gather elastic members 63a and 63b, the parts that the gather elastic members 63a and 63b are not fixed to the gather sheet 62 although the gather elastic members 63a and 63b are included, and the gather elastic members 63a and 63b are finely cut and hardly expand or contract.

As described above, in the rising portion 68, if the middle of the front-back direction LD including the crotch portion is the main region 68Z, the basic part of the rising gather 60 comes into contact with the body surface at a shallower angle and rises higher with a narrower width. Further, the rising portion 68 has the support region 68P formed only by the third part 60C extending toward the center in the width direction between the main region 68Z and the back fallen portion 67B. Further, the tip end side of the third part 60C is contracted by the second gather elastic member 63b, and it is extensible in the front-back direction LD together with the second gather elastic member 63b, and the base edge side of the third part 60C is the non-stretchable portion 69. As a result, the tip end side (width direction center side) of the third part 60C rises up with respect to the base edge side. Here, the third part 60C of the support region 68P has a layer that follows the second part 60B of the main region 68Z, such that a force is transmitted in those parts as a continuous part. Therefore, as the tip end side of the third part 60C (width direction center side) rises up with respect to the base edge side, in the portion of the second part 60B of the main region 68Z near the support region, the position on the base edge side (width direction center side) is high, and the rising angle is small. As a result, compared to the case without a support region 68P, the rising gather 60 (the main region 68Z of the gather) is suitable for wearing, that is, it makes contact with the body surface at a shallower angle and tends to rise higher with a narrow width, and the state is easily maintained. On the other hand, the support region 68P forms a pocket between the third part 60C and the surface facing below the third part 60C, and the pocket is less likely to be crushed as compared with the conventional one in which the entire front-back direction LD of the rising portion 68 is the main region 68Z. By having such the support region 68P, it is possible to temporarily store an excrement that has rushed to a position close to the back fallen portion 67B and to improve the prevention of the excrement from leaking at a site near the back fallen portion 67B.

The structures of the first part 60A and the second part 60B of the main region 68Z and the third part 60C of the support region 68P are not particularly limited. However, it is preferable that the gather sheets 62 forming the rising gathers 60 have the same folded structure and are continuous over the entire front-back direction LD since continuous production can be performed in a general production line. For this reason, in the illustrated example, the third part 60C includes a first support portion 62a that follows the first part 60A of the main region 68Z (in the same layered structure), and a second support portion 62b that follows the second part 60B of the main region 68Z (in the same layered structure), and at least the tip end portion of the second support portion 62b is formed by being stacked and integrated with the first support portion 62a with a hot melt adhesive HM or the like. With this structure, while continuing the gather sheet 62 with the same folded structure from the front fallen portion 67F to the back fallen portion 67B, the support region 68P, that is, the third part 60C extending only toward the center in the width direction, can be provided only by adding an adhesive to the site to be the support region 68P. Further, when at least the tip end portion of the second support portion 62b is stacked and integrated with the first support portion 62a, in the portion of the second part 60B of the main region close to the support region 68P, the position of the base edge side (width direction center side) is higher than the tip end side, and the rising angle with respect to the width direction becomes negative. As a result, (main regions 68Z of) the rising gathers 60 are not easily fallen inward, and therefore are more likely to be in an appropriate wearing state at the time of wearing, and the wearing state is more easily maintained. The bonded portion between the second support portion 62b and the first support portion 62a is preferably the non-stretchable portion 69.

FIGS. 11 to 14 illustrate other examples of the rising gather 60, and the examples are same as the examples illustrated in FIGS. 3, 4, 8(a), and 9 in that one gather sheet 62 is formed by folding back, but is different in the folded structure of the gather sheet 62. That is, as illustrated in the enlarged view of FIG. 14, the second part 60B of the main region 68Z is formed by stacking and integrating the first layer 61a extending outward in the width direction from the tip of the first part 60A, the second layer 61b extending inward in the width direction from the tip of the first layer 61a, and the third layer 61c extending outward in the width direction from the tip end of the second layer 61b by a hot melt adhesive HM or the like. Then, in the support region 68P, a portion 61d that follows the first layer 61a of the main region 68Z and a portion 61g that follows the first part 60A of the main region 68Z are fixed to the top sheet 30 with the hot melt adhesive HM or the like in a fallen state. Further, the third part 60C has a first support layer 61e that follows the second layer 61b of the main region 68Z, and a second support layer 61f that follows the third layer 61c of the main region 68Z. At least the tip end portion of the second support layer 61f is formed by being stacked and integrated with the first support layer 61e. Although this structure is somewhat complicated, not only is the gather sheet 62 continuous with the same folded structure over the entire front-back direction LD of the rising gather 60, but there is an advantage that the number of layers of the third part 60C can be reduced to make the part flexible. For example, in the rising gather 60 in the illustrated example, the first part 60A of the main region 68Z is composed of only one gather sheet 62. The second part 60B has a three-layered structure in which the first part 60A is folded back three times and stacked and integrated, and the third part 60C has a two-layered structure. Further, when at least the tip end portion of the second support layer 61f is stacked and integrated with the first support layer 61e, in the portion of the second part 60B of the main region 68Z close to the support region 68P, the position of the base edge side (width direction center side) is higher than the tip end side, and the rising angle with respect to the width direction becomes negative. As a result, (main regions of) the rising gathers 60 are more likely to be in an appropriate wearing state at the time of wearing, and the wearing state is more easily maintained. The bonded portion between the second support layer 61f and the first support layer 61e is preferably the non-stretchable portion 69.

In addition, in the examples illustrated in FIGS. 11 to 14, the root portion 65 is provided on the side surface of the inner member 200, but as in the examples illustrated in FIGS. 3, 4, 8(a), and 9, the inner member 200 may have the root portion 65 on the back surface of the side portion. In addition, in the example illustrated in FIGS. 11 to 14, the gather sheet 62 extends laterally from the root portion 65 to form a bulging portion 70 bulging laterally of the absorber 56. Further, the bulging portion 70 has a two-layered structure by attaching the back surface side sheet 72, and a lifting elastic member 73 is provided between the layers. As a result, the bulging portion 70 forming the side portion of the inner member 200 is lifted to the wearer's skin side by contraction force of the lifting elastic member 73. However, this bulging portion 70 can be omitted.

It is also proposed that, as illustrated in FIGS. 15 and 16, the support region 68P includes the third part 60C extending outward in the width direction, and the fourth part 60D extending inward in the width direction from the tip end of the third part 60C, the second gather elastic member 63b of the support region 68P is attached to at least the tip end of the fourth part 60D along the front-back direction LD, the tip end side of the fourth part 60D is contracted by the second gather elastic member 63b and is extensible in the front-back direction LD together with the second gather elastic member 63b, the part extending from the third part 60C to the base edge side of the fourth part 60D extends is the non-stretchable portion 69, and the fourth part 60D has a layer that follows the second part 60B of the main region 68Z. That is, in this case, the tip end side (width direction outer side) of the third part 60C rises with respect to the base edge side, and the tip end side (width direction center side) of the fourth part 60D rises with respect to the base edge side with the tip edge side of the third part 60C as a base. Here, the fourth part 60D of the support region 68P has a layer that follows the second part 60B of the main region 68Z, such that a force is transmitted in those parts as a continuous part. Therefore, as the tip end side of the fourth part 60D (width direction center side) rises up with respect to the base edge side, in the portion of the second part 60B of the main region 68Z near the support region 68P, the position on the base edge side (width direction center side) is high, and the rising angle is small. As a result, compared to the case without a support region 68P, the rising gather 60 (the main region of the gather) is suitable for wearing, that is, it makes contact with the body surface at a shallower angle and tends to rise higher with a narrow width, and the state is easily maintained. Further, the support region 68P has a pocket (accommodation space) between the third part 60C and the fourth part 60D, the entrance of the pocket can be expanded higher, and the depth of the pocket is less likely to be shallow.

Figure 12:
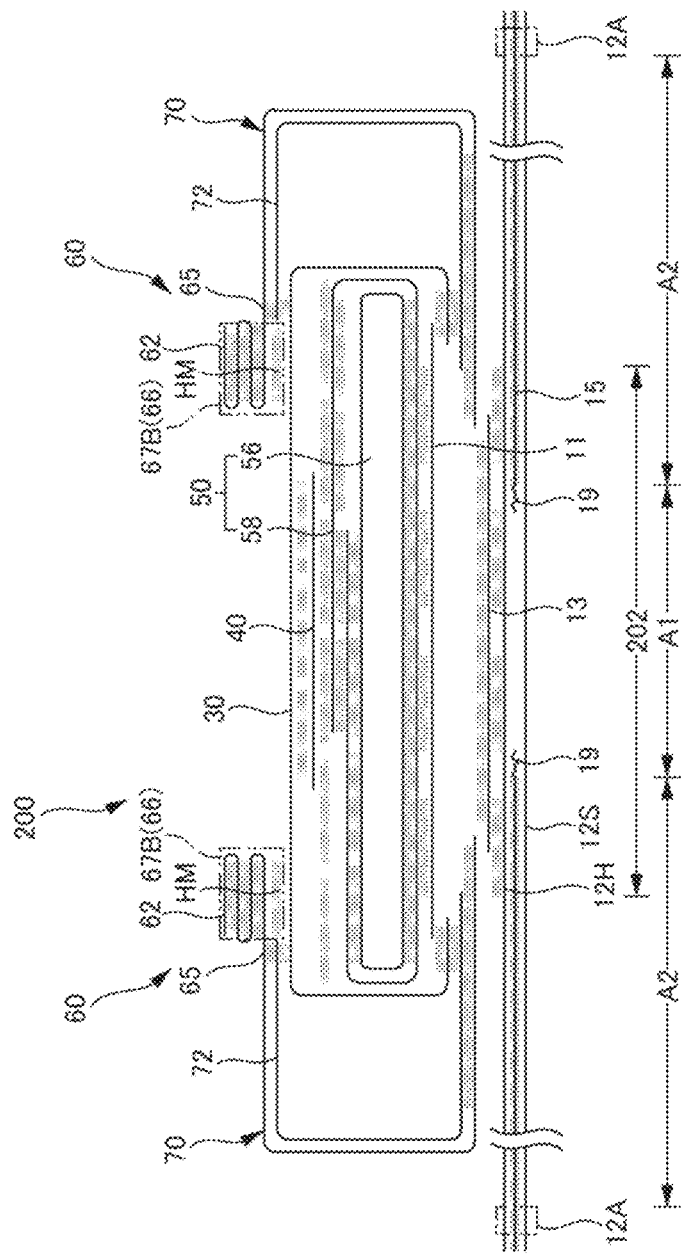
FIG. 12 is a cross-sectional view passing through a fallen portion in another example.
Figure 13:
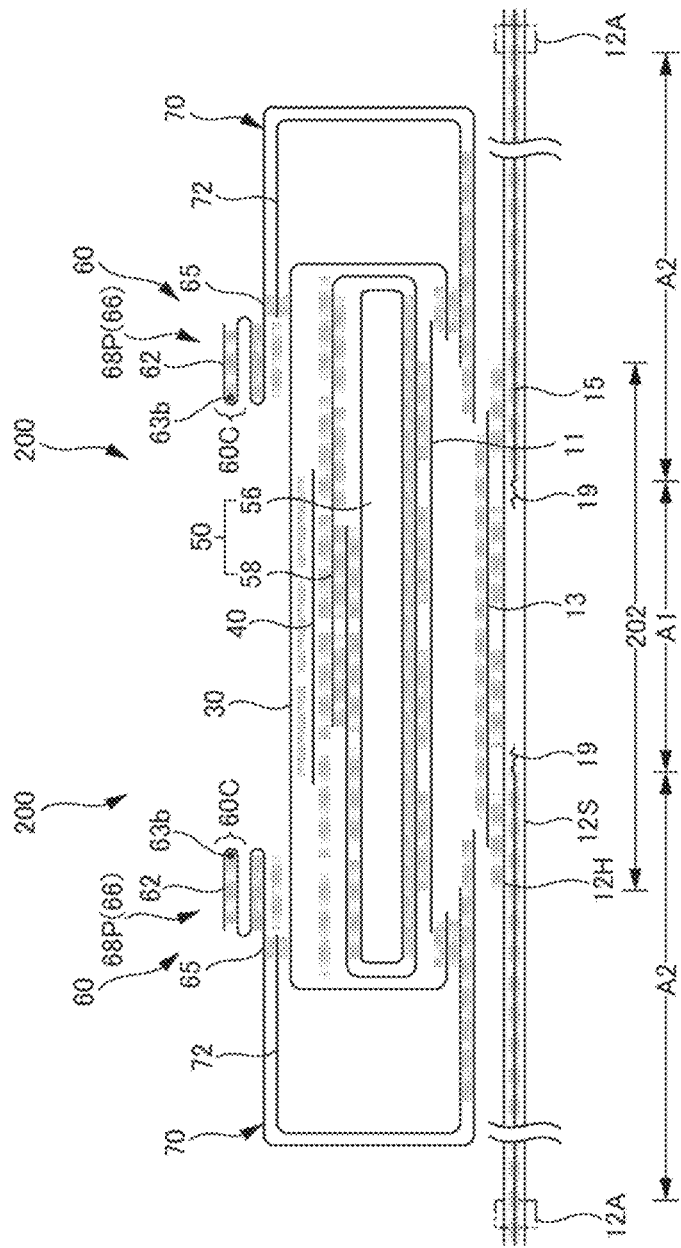
FIG. 13 is a cross-sectional view passing through a support region in another example.

The structures of the first part 60A and the second part 60B of the main region 68Z and the third part 60C and the fourth part 60D of the support region 68P are not particularly limited. However, it is preferable that the gather sheets 62 forming the rising gathers 60 have the same folded structure and are continuous over the entire front-back direction LD since continuous production can be performed in a general production line. Therefore, in this example, the main region 68Z similar to the example illustrated in FIGS. 11, 12, and 14(a) is provided. That is, the second part 60B of the main region 68Z is formed by stacking and integrating the first layer 61a extending outward in the width direction from the tip end of the first part 60A, the second layer 61b extending inward in the width direction from the tip end of the first layer 61a, and the third layer 61c extending outward in the width direction from the tip of the second layer 61b by a hot melt adhesive HM or the like. Further, in the support region 68P, the portion 61g that follows the first part 60A of the main region 68Z is fixed to the top sheet 30 in a fallen state by the hot melt adhesive HM or the like. The fourth part 60D has the first support layer 61e that follows the second layer 61b of the main region 68Z and the second support layer 61f that follows the third layer 61c of the main region 68Z. At least the tip end portion of the second support layer 61f is formed by being stacked and integrated with the first support layer 61e by the hot melt adhesive HM or the like. The third part 60C is formed by the third support layer 61d that follows the first support layer 61e of the main region 68Z, and the first support layer 61e and the third support layer 61D are not bonded. The second gather elastic member 63b may be arranged at a portion other than the tip end portion of the fourth part 60D. From this viewpoint, the number of the second gather elastic members 63b is preferably one or two, and is preferably provided at a position near the tip of the fourth part 60D. Others are the same as the above-described example.

Although a material of the gather sheet 62 is not particularly limited, a nonwoven fabric which is flexible and excellent in uniformity and concealing property such as a spunbonded nonwoven fabric (SS, SSS, etc.), SMS nonwoven fabric (SMS, SSMMS, etc.), meltblown nonwoven fabric, and on which a water repellent process is performed by silicon as necessary, can be preferably used, and the fiber basis weight is preferably set to about 10 to 30 g/m². As the gather elastic members 63a and 63b, a rubber thread or the like can be used. When a spandex rubber thread is used, the fineness is preferably 470 to 1240 dtex, more preferably 620 to 940 dtex. The stretch rate at the time of fixing is preferably from 150 to 350%, more preferably from 200 to 300%. As illustrated in the drawing, a waterproof film 64 may be interposed between the gather sheet 62 folded in two, and in this case, the gather sheet 62 may be partially omitted in the portion where the waterproof film 64 is present. However, in order to make the appearance and feel of the product like a cloth, it is necessary that at least the outer surface from the base edge to the tip of the rising gathers 60 is formed of the gather sheet 62 as the illustrated embodiment.

At least one of hot melt adhesives by various application methods and a fixing means by material welding such as a heat sealing, ultrasonic sealing, and the like can be used for bonding between layers of the gather sheets 62 and fixing the gather elastic members 63a and 63b sandwiched therebetween. When the entirely surfaces of layers of the gather sheet 62 are bonded together, the flexibility is impaired. Therefore, it is preferable that the portions other than the adhesive portions of the gather elastic members 63a and 63b are not adhered or are weakly adhered. In the illustrated embodiment, by applying a hot melt adhesive only to the outer peripheral surfaces of the gather elastic members 63a and 63b by an application means such as a comb gun or a sure wrap nozzle and sandwiching them between layers of the gather sheets 62, fixing of the gather elastic members 63a and 63b to the gather sheet 62 and fixing between layers of the gather sheets 62 are carried out by using only a hot melt adhesive applied to the outer peripheral surface of the gather elastic members 63a and 63b.

Similarly, at least one of the hot melt adhesive HM by various application methods and a means by material welding such as a heat sealing, ultrasonic sealing and the like can be used for fixing the waterproof film 64 built in the rising gather 60 and the gather sheet 62 and fixing the fallen portion 67.

Although the dimension of the rising gather 60 is appropriately determined, in the case of an infant use, as illustrated in FIG. 3, for example, the standing height of the rising gathers 60 (length in the width direction of the main unit section 66 in the spread state) W2 is preferably 15 to 60 mm, in particular 20 to 40 mm. Further, in a state where the rising gathers 60 are folded flat so as to be parallel to the surface of the top sheet 30, the distance W1 between the innermost folds is preferably from 60 to 190 mm, in particular from 70 to 140 mm. In the case of adult use, the standing height (length in the width direction of the main unit section 66 in the spread state) W2 of the rising gathers 60 is preferably 20 to 60 mm, particularly 30 to 55 mm. Further, in a state where the rising gathers 60 are folded flat so as to be parallel to the surface of the top sheet 30, the distance W1 between the innermost folds is preferably from 110 to 190 mm, in particular from 120 to 150 mm.

The front fallen portion 67F and the back fallen portion 67B have the same folding structure as the main region 68Z and the support region 68P in the main unit section 66, but are fixed in a folded state. As for the front fallen portion 67F and the back fallen portion 67B, the main unit section 66 may be fixed to the side surface of the top sheet 30 with a hot melt adhesive HM or the like, as in the example illustrated in FIG. 12. In addition, as illustrated in FIGS. 1, 5, 8, and 10, when the cover sheet layer 12r extending over the entire width direction of the outer members 12F and 12B is provided from the end on the waist opening WO side on the inner surface of the outer member 12F and 12B to the position overlapping the end portion on the waist opening WO side of the inner member 200, the cover sheet layer 12r can be used to fix the front fallen portion 67F and the back fallen portion 67B. That is, it is also preferable that, as illustrated in FIG. 10, a portion of the cover sheet layer 12r that overlaps with the inner member 200 and portions on both sides in the width direction thereof is bonded to the surfaces that face the back surface side (the inner surface of the outer member, the surface of the inner member 200, the rising gather 60) by the hot melt adhesive HM or the like, and consequently, the portion of the rising gather 60 crushed in the thickness direction by the cover sheet layer 12r be a fallen portion (the back fallen portion 67B in FIG. 10). As a result, the fallen region is only a portion overlapping the cover sheet layer 12r, and not only is it shortened, but also the step of fixing the fallen portion is not needed. Further, since the fallen portion is not bonded to the top sheet 30, an excrement reaching a pocket of the support region 68P easily penetrates under the fallen portion. As a result, prevention of excrement leakage in sites near the fallen portion will be further improved.

<Others>

The support region 68P is provided only on the back side in the example illustrated in FIG. 8(a), but instead of or together with this, as illustrated in FIG. 8(b), the support region 68P can be provided also in the front side (that is a site adjacent to the front fallen portion 67F).

<Explanation of Terms Used Herein>

The following terms in the specification have the following meanings unless otherwise specified in the specification.

"Front-back direction" means the direction indicated by the reference character LD in the drawings (longitudinal direction), and "width direction" means the direction indicated by WD in the drawings (left-right direction), and the front-back direction and the width direction are orthogonal to each other.

"Front surface side" means a side close to the skin of a wearer wearing an underpants-type disposable diaper. "Back surface side" means a side far from the skin of a wearer wearing an underpants-type disposable diaper.

"Front surface" means a surface of a member close to the skin of a wearer wearing an underpants-type disposable diaper. "Back surface" means a surface far from the skin of a wearer wearing an underpants-type disposable diaper.

"Area ratio" means a ratio of a target portion to a unit area, and a total area of target portions (for example, holes) in a target region (for example, a cover nonwoven fabric) is divided by the area of the target region and expressed as a percentage. In a form in which a large number of target portions are provided at intervals, it is desirable to set the target region to a size such that ten or more target portions are included and obtain the area ratio. For example, the area ratio of the holes can be measured by the following procedure, for example, using the trade name VHX-1000 manufactured by KEYENCE Co., Ltd. under measurement conditions of 20 times.

(1) Set lens to 20× magnification and adjust focus. Adjust the position of a nonwoven fabric such that a hole fits 4×6.
(2) Specify the brightness of the region of the hole and measure the area of the hole.
(3) Click the color extraction of "Area measurement" in "Measurement/Comment". Click on the hole part.
(4) Click "Batch measurement", check "Show measurement result window" and save with CSV data.

"Stretch rate" means the value when the natural length is taken as 100%. For example, a stretch rate of 200% is synonymous with a stretch magnification of 2 times.

"Gel strength" is measured as follows: A super absorbent polymer 1.0 g is added to artificial urine (mixture of urea: 2 wt %, sodium chloride: 0.8 wt %, calcium chloride dihydrate: 0.03 wt %, magnesium sulfate heptahydrate: 0.08 wt %, and ion exchanged water: 97.09 wt %) 49.0 g, and stirred with a stirrer. After leaving generated gel for three hours in a thermo-hygrostat bath at 40° C.×60% RH, return to room temperature, and measure the gel strength with a card meter (Curdmeter-MAX ME-500, manufactured by I. techno Engineering).

"Basis weight" is measured as follows. After preliminary drying a sample or a test piece, the sample or the test piece is left in a test chamber or equipment in the standard state (the test location is at a temperature of 23±1° C. and with a relative humidity of 50±2%) to be constant weight. The preliminary drying refers to making a sample or a test piece a constant weight in an environment at a temperature of 100° C. For fibers with an official moisture regain of 0.0%, preliminary drying may not be performed. A sample of dimensions of 100 mm×100 mm is cut using a template for sampling (100 mm×100 mm) from a test piece in a constant weight. The basis weight is set by weighing the sample, multiplying by 100, and calculating the weight per one square meter.

"Thickness" is automatically measured under the conditions of a load of 0.098 N/cm$^2$ and a pressing area of 2 cm$^2$ using an automatic thickness measuring device (KES-G5 handy compression measuring program).

"Water absorption capacity" is measured according to JIS K7223-1996 "Test method for water absorption capacity of super absorbent polymer".

"Water absorption rate" is the "time to end point" when JIS K7224-1996 "Test method for water absorption rate of super absorbent polymer" has been carried out using 2 g of super absorbent polymer and 50 g of physiological saline solution.

"Unfolded state" means a flatly spread state without shrinkage or slackness.

The dimension of each part means the dimension in the spread state, not the natural length state, unless otherwise stated.

When environmental conditions in tests and measurements are not described, the tests and measurements shall be carried out in a test room or apparatus in a standard state (a temperature of 23±1° C. and a relative humidity of 50±2% at the test location).

INDUSTRIAL APPLICABILITY

The present invention can be applied to disposable diapers in general, such as tape-type disposable diapers as in the above example, underpants-type disposable diapers and pad-type disposable diapers, and it is obvious that the present invention can also be applied to other disposable wearing articles such as sanitary napkins.

REFERENCE SIGNS LIST

A1 non-stretchable region
A2 stretchable region
L intermediate region
LD front-back direction
T lower torso region
U under-waist portion
W waist portion
WO waist opening
11 liquid impervious sheet
12B back outer member
12E waist extended section
12F front outer member
12H inner sheet layer
12S outer sheet layer
12r cover sheet layer
13 cover nonwoven fabric
17 waist portion elastic member
18 ideal elastic member
30 top sheet
40 intermediate sheet
50 absorbent element
56 absorber
58 package sheet
60 rising gather
60A first part
60B second part
60C third part
60D fourth part
61a first layer
61b second layer
61c third layer
62 gather sheet
62a first support portion
62b second support portion
63a, 63b gather elastic member
63a first gather elastic member
63b second gather elastic member
65 root portion
66 main unit section
67B back fallen portion
67F front fallen portion
68 rising portion
68P support region
68Z main region
69 non-stretchable portion
200 inner member
201, 202 inner and outer joined portion

The invention claimed is:

1. A disposable wearing article, comprising:
rising gathers rising from each side in a width direction,
wherein each rising gather has a root portion fixed to the disposable wearing article, a main unit section extending from the root portion, a front fallen portion formed by fixing a front end portion of the main unit section in a fallen state and a back fallen portion formed by fixing a back end portion of the main unit section in a fallen state, and a non-fixed rising portion located between the front fallen portion and the back fallen portion of the main unit section,
the non-fixed rising portion has:
a main region composed only of a first part extending toward a center in the width direction without being folded back and a second part extending outward in the width direction from a tip end of the first part located closer to the center in the width direction without being folded back so as to be located above the first part, in a middle in a front-back direction including a crotch portion, and
a support region composed only of a third part extending toward the center in the width direction without being folded back, between the main region and at least one of the front fallen portion and the back fallen portion,
the first part is not fixed to a surface facing and located below the first part, the second part is not fixed to a surface of the first part facing thereto, and the third part is not fixed to a surface facing and located below the third part,
the main region has a first gather elastic member attached to at least a tip end of the second part located outward in the width direction and extending along the front-back direction,
in the main region, the tip end of the second part is contracted by the first gather elastic member and is extensible in the front-back direction together with the first gather elastic member, so that the first part is raised with respect to the surface facing and located below the first part with increasing distance therebetween toward the center side in the width direction and the second part is raised with respect to the surface of the first part facing thereto with increasing distance therebetween outward in the width direction,
the support region has a second gather elastic member attached to at least a tip end of the third part located closer to the center in the width direction and extending along the front-back direction,
in the support region, a center side in the width direction of the third part is contracted by the second gather elastic member and is extensible in the front-back direction together with the second gather elastic member, and an outward side in the width direction of the third part is a non-stretchable portion, so that the third part is raised with respect to the surface facing and located below the third part with increasing distance therebetween toward the center side in the width direction, and
the third part has a layer that follows the second part of the main region.

2. The disposable wearing article according to claim 1, wherein the third part has a first support portion that follows the first part of the main region, and a second support portion that follows the second part of the main region, and at least a tip end of the second support portion is stacked and integrated with the first support portion.

3. The disposable wearing article according to claim 2, which is an underpants-type disposable wearing article,
wherein a front outer member forming at least a lower torso portion of a front body and a back outer member forming at least a lower torso portion of a back body are separately provided, the front outer member and the back outer member are separated in the front-back direction,
an inner member containing an absorber extends in the front-back direction from the front outer member to the back outer member, and is bonded to the front outer member and the back outer member, respectively,
a side seal portion in which both side portions of the front outer member and both side portions of the back outer member are bonded, a waist opening and a pair of left and right leg openings are provided,
the inner member has rising gathers rising from each side, and
the main region is continuous from the front outer member to the back outer member.

4. The disposable wearing article according to claim 1, wherein, the second part of the main region is formed by stacking and integrating a first layer extending outward in the width direction from a tip end of the first part located closer to the center in the width direction, a second layer extending inward in the width direction from a tip end of the first layer, and a third layer extending outward in the width direction from a tip end of the second layer,
in the support region, a portion that follows the first layer of the main region and a portion that follows the first part of the main region are fixed in a fallen state, the third part has a first support layer that follows the second layer of the main region and a second support layer that follows the third layer of the main region, and at least a tip end of the second support layer is stacked and integrated with the first support layer.

5. The disposable wearing article according to claim 4, which is an underpants-type disposable wearing article,
wherein a front outer member forming at least a lower torso portion of a front body and a back outer member forming at least a lower torso portion of a back body are separately provided, the front outer member and the back outer member are separated in the front-back direction,
an inner member containing an absorber extends in the front-back direction from the front outer member to the back outer member, and is bonded to the front outer member and the back outer member, respectively,
a side seal portion in which both side portions of the front outer member and both side portions of the back outer member are bonded, a waist opening and a pair of left and right leg openings are provided,
the inner member has rising gathers rising from each side, and
the main region is continuous from the front outer member to the back outer member.

6. The disposable wearing article according to claim 1, which is an underpants-type disposable wearing article,
wherein a front outer member forming at least a lower torso portion of a front body and a back outer member forming at least a lower torso portion of a back body are separately provided, the front outer member and the back outer member are separated in the front-back direction,
an inner member containing an absorber extends in the front-back direction from the front outer member to the back outer member, and is bonded to the front outer member and the back outer member, respectively, a side seal portion in which both side portions of the front outer member and both side portions of the back outer member are bonded, a waist opening and a pair of left and right leg openings are provided, the inner member has rising gathers rising from each side, and the main region is continuous from the front outer member to the back outer member.

7. A disposable wearing article, comprising:

rising gathers rising from each side in a width direction, wherein each rising gather has a root portion fixed to the disposable wearing article, a main unit section extending from the root portion, a front fallen portion formed by fixing a front end portion of the main unit section in a fallen state and a back fallen portion formed by fixing a back end portion of the main unit section in a fallen state, and a non-fixed rising portion located between the front fallen portion and the back fallen portion of the main unit section, the non-fixed rising portion has:
  a main region composed only of a first part extending toward a center in the width direction without being folded back and a second part extending outward in the width direction from a tip end of the first part located closer to the center in the width direction without being folded back so as to be located above the first part, in a middle in a front-back direction including a crotch portion, and
  a support region composed only of a third part extending outward in the width direction without being folded back and a fourth part extending inward in the width direction from a tip end of the third part located outward in the width direction without being folded back so as to be located above the third part, in a site adjacent to at least one of the front fallen portion and the back fallen portion, the first part is not fixed to a surface facing and located below the first part, the second part is not fixed to a surface of the first part facing thereto, the third part is not fixed to a surface facing and located below the third part, and the fourth part is not fixed to a surface of the third part facing thereto, the main region has a first gather elastic member attached to at least the tip end of the second part located outward in the width direction and extending along the front-back direction, in the main region, the tip end of the second part is contracted by the first gather elastic member and is extensible in the front-back direction together with the first gather elastic member, so that the first part is raised with respect to the surface facing and located below the first part with increasing distance therebetween toward the center side in the width direction and the second part is raised with respect to the surface of the first part facing thereto with increasing distance therebetween outward in the width direction, the support region has a second gather elastic member attached to at least a tip end portion of the fourth part located closer to the center in the width direction and extending along the front-back direction, in the support region, a center side in the width direction of the fourth part is contracted by the second gather elastic member and is extensible in the front-back direction together with the second gather elastic member, and a portion from the third part over an outward side in the width direction of the fourth part is a non-stretchable portion, so that the third part is raised with respect to the surface facing and located below the third part with increasing distance therebetween outward in the width direction, and the fourth part is raised with respect to the third part with increasing distance therebetween toward the center side in the width direction, and the fourth part has a layer that follows the second part of the main region.

8. The disposable wearing article according to claim 7, wherein the second part of the main region is formed by stacking and integrating a first layer extending outward in the width direction from a tip end of the first part located closer to the center in the width direction, a second layer extending inward in the width direction from a tip end of the first layer, and a third layer extending outward in the width direction from a tip end of the second layer, in the support region, a portion that follows the first part of the main region is fixed in a fallen state, the fourth part has a first support layer that follows the second layer of the main region and a second support layer that follows the third layer of the main region, and at least a tip end of the second support layer is stacked and integrated with the first support layer, and the third part is formed by a third support layer that follows the first layer of the main region, and the first support layer and the third support layer are not bonded.

9. The disposable wearing article according to claim 8, which is an underpants-type disposable wearing article, wherein a front outer member forming at least a lower torso portion of a front body and a back outer member forming at least a lower torso portion of a back body are separately provided, the front outer member and the back outer member are separated in the front-back direction, an inner member containing an absorber extends in the front-back direction from the front outer member to the back outer member, and is bonded to the front outer member and the back outer member, respectively, a side seal portion in which both side portions of the front outer member and both side portions of the back outer member are bonded, a waist opening and a pair of left and right leg openings are provided, the inner member has rising gathers rising from each side, and the main region is continuous from the front outer member to the back outer member.

10. The disposable wearing article according to claim 7, which is an underpants-type disposable wearing article, wherein a front outer member forming at least a lower torso portion of a front body and a back outer member forming at least a lower torso portion of a back body are separately provided, the front outer member and the back outer member are separated in the front-back direction, an inner member containing an absorber extends in the front-back direction from the front outer member to the back outer member, and is bonded to the front outer member and the back outer member, respectively, a side seal portion in which both side portions of the front outer member and both side portions of the back outer member are bonded, a waist opening and a pair of left and right leg openings are provided, the inner member has rising gathers rising from each side, and the main region is continuous from the front outer member to the back outer member.

\* \* \* \* \*